United States Patent
Cohen et al.

(10) Patent No.: US 11,583,542 B2
(45) Date of Patent: Feb. 21, 2023

(54) COMPOSITIONS OF BILE ACIDS AND PHENYLBUTYRATE COMPOUNDS

(71) Applicant: Amylyx Pharmaceuticals Inc., Cambridge, MA (US)

(72) Inventors: Joshua Cohen, Canton, MA (US); Justin Klee, Cambridge, MA (US); David Wai Fung Ma, Whitby (CA)

(73) Assignee: Amylyx Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/940,102

(22) Filed: Jul. 27, 2020

(65) Prior Publication Data

US 2021/0177867 A1    Jun. 17, 2021

Related U.S. Application Data

(60) Provisional application No. 62/948,756, filed on Dec. 16, 2019, provisional application No. 63/030,793, filed on May 27, 2020.

(51) Int. Cl.

| | | |
|---|---|---|
| *A61K 31/4709* | (2006.01) | |
| *A61K 9/06* | (2006.01) | |
| *A61K 47/10* | (2017.01) | |
| *A61K 47/12* | (2006.01) | |
| *A61P 17/10* | (2006.01) | |
| *A61P 17/00* | (2006.01) | |
| *A61P 17/04* | (2006.01) | |
| *A61P 31/04* | (2006.01) | |
| *A61K 31/575* | (2006.01) | |
| *A61K 47/02* | (2006.01) | |
| *A61K 31/192* | (2006.01) | |
| *A61K 47/26* | (2006.01) | |

(52) U.S. Cl.
CPC .......... *A61K 31/575* (2013.01); *A61K 31/192* (2013.01); *A61K 47/02* (2013.01); *A61K 47/26* (2013.01)

(58) Field of Classification Search
CPC ........................... A61K 9/4808; A61K 31/575
USPC .......................................................... 514/340
See application file for complete search history.

(56) References Cited

U.S. PATENT DOCUMENTS

| | | |
|---|---|---|
| 7,737,175 B2 | 6/2010 | Yao et al. |
| 9,632,075 B2 | 4/2017 | Leong et al. |
| 9,872,865 B2 | 1/2018 | Cohen et al. |
| 10,251,896 B2 | 4/2019 | Cohen et al. |
| 10,857,162 B2 | 12/2020 | Cohen et al. |
| 11,071,742 B2 | 7/2021 | Cohen et al. |
| 2006/0135612 A1 | 6/2006 | Ferrante |
| 2009/0312297 A1 | 12/2009 | Hotamisligil et al. |
| 2011/0142799 A1 | 6/2011 | Glimcher et al. |
| 2012/0157419 A1 | 6/2012 | Gilat et al. |
| 2014/0288030 A1 | 9/2014 | Cohen et al. |
| 2016/0022684 A1 | 1/2016 | Kuo et al. |
| 2018/0098999 A1 | 11/2018 | Cohen et al. |
| 2019/0255072 A1 | 8/2019 | Cohen et al. |
| 2020/0171052 A1 | 6/2020 | Cohen et al. |
| 2020/0230156 A1 | 7/2020 | Cohen et al. |
| 2022/0110948 A1 | 4/2022 | Cohen et al. |
| 2022/0117978 A1 | 4/2022 | Cohen et al. |
| 2022/0160733 A1 | 5/2022 | Cohen et al. |

FOREIGN PATENT DOCUMENTS

| | | |
|---|---|---|
| CN | 101048164 | 10/2007 |
| EP | 2422787 | 8/2010 |
| EP | 2599477 | 6/2013 |
| EP | 3016654 | 9/2018 |
| JP | 2005532372 | 10/2005 |
| JP | 2008-518935 | 6/2008 |
| JP | 2011518119 | 6/2011 |
| WO | WO 2004/096123 | 11/2004 |
| WO | WO 2006/050165 | 5/2006 |
| WO | WO 2006/086452 | 8/2006 |
| WO | WO 2009/140265 | 11/2009 |
| WO | WO 2013/142490 | 9/2013 |
| WO | WO 2014/158547 | 10/2014 |
| WO | WO 2015/001379 | 1/2015 |
| WO | WO 2021/126870 | 6/2021 |

OTHER PUBLICATIONS

Davies et al. ("Oral solid dosage forms", in Gibson, M., Pharmaceutical Preformulation and Formulation, Interpharm, Colorado, 2001). (Year: 2001).*

Amylyx Pharmaceuticals Inc (Evaluation of the Safety, Tolerability, Efficacy and Activity of AMX0035, a Fixed Combination of Phenylbutyrate (PB) and Tauroursodeoxycholic Acid (TUDCA), for Treatment of(ALS) for the Treatment of ALS Study (Protocol Version 6.0 Jan. 11, 2019) (Year: 2019).*

[No Author] "Safety and Efficacy of TR019622 as add-on Therapy to Riluzole Versus Placebo in Treatment of Patients Suffering From ALS (Mitotarget)," U.S. Library of Medicine, Mar. 24, 2009, NCT00868166.

[No Author] "Experimental Alzheimer Drags Targeting Beta-Amyloid and the Amyloid Hypothesis," Alzheimer's Associate, 2007, 3 pages.

[No Author] "Know the 16 Signs, Early Detection Matters," Alzheimer's Association, 2009, 2 pages.

[Noauthor] "Alzheimer's Disease and Type 2 Diabetes: What is the Link?" Alzheimer's Association, 2011, 3 pages.

Afanas'ev, "Signaling and Damaging Functions of Free Radicals in Aging—Free Radical Theory, Hormesis, and TOR," Aging and Dis., Oct. 2010, 1(2):75-88.

Al-Chalabi et al., "Protocol for a double-blind randomised placebo controlled trial of lithium carbonate in patients with amyotrophic Lateral Sclerosis," BMC Neurology, 2011, 11:111.

Aldini et al., "Relationship between structure and intestinal absorption of bile acids with a steroid or side-chain modification," Steroids, 1996, 61:590-597.

(Continued)

*Primary Examiner* — Layla Soroush
(74) *Attorney, Agent, or Firm* — Fish & Richardson P.C.

(57) ABSTRACT

The present disclosure relates to compositions including a phenylbutyrate compound and a bile acid, and methods of processing such compositions.

21 Claims, 14 Drawing Sheets

(56) References Cited

OTHER PUBLICATIONS

Al-Hashemi et al., "A review on the angle of repose of granular materials," Powder Technology, May 1, 2018, 330:397-417.

ALSUtangled Group, "ALSUntangled No. 25: Ursodiol," Amyotroph Lateral Scler Frontotemporal Degener., 2014, 15(5-6):475-478.

Amaral et al., "Bile acids: regulation of apoptosis by ursodeoxycholic Acid," J Lipid Res., 2009, 50:1721-1734.

Andersen et al., "EFNS guidelines on the Clinical Management of Amyotrophic Lateral Sclerosis (MALS)—revised report of an EFNS task force," European Journal Neurology, 2012, 19:360-375.

AU Office Action in Australian Application No. 2014242123, dated Feb. 22, 2018, 4 pages.

AU Office Action in Australian Appln. No. 2019200658, dated Mar. 13, 2020, 8 pages.

Axcan Pharma US Inc.: Treatment of Patients With All Stages of Primary Biliary Cirrhosis; URSO (ursodiol) Tablets, 250 mg; Medical Officer's Review; NDA 20-675; Mar. 26, 1996.

Basseri et al., "The chemical chaperone 4-phenylbutyrate inhibits adipogenesis by modulating the unfolded protein response," J Lipid Res., 2009, 50:2486-2501.

Berger et al., "Structure-function analysis of the tertiary bile acid TUDCA for the resolution of endoplasmic reticulum stress in intestinal epithelial cells," Biochemical and Biophysical Research Communications, 2011, 409:610-615.

Berry et al., "Design and Initial Results of a Multi-Phase Randomized Trial of Ceftriaxone in Amyotrophic Lateral Sclerosis," PLoS ONE, 2013, 8(4):e61177.

Biosciences Inc., Phenylbutyrate Na Inducer, Catalog# SIH-255, StressMarq, 2011, 2 pages.

CA Office Action in Canadian Appln. No. 2,908,683, dated Mar. 12, 2020, 5 pages.

Castro et al., "The Bile Acid Tanroursodeoxycholic Acid Modulates Phosphorylation and Translocation of Bad via Phosphatidylinositol 3-Kinase in Glutamate-Induced Apoptosis of Rat Cortical Neurons," JPET, 2004, 311:845-852.

Chiu et al., "Hepatitis C Virus Infection Increases the Risk of Alzheimer's Diseases: A Population-Based Cohort Study in Taiwan," Poster, 2013, 1 page.

Clinical Trials.gov: "Efficacy and Tolerability of Tauroursodeoxycholic Acid in Amyotrophic Lateral Sclerosis (TUDCA-ALS)", ClinicalTrials.gov, Mar. 23, 2012, 22 pages.

CN Office Action Chinese Application No. 201480017771X, First Office Action, dated Dec. 14, 2016, 13 pages (with translation).

CN Office Action in Chinese Application No. 201480017771.X, dated Feb. 24, 2018, 10 pages (with English translation).

CN Office Action in Chinese Application No. 201480017771.X, dated Nov. 8, 2018, 15 pages (with English translation).

Cudkowicz et al., "Phase 2 study of sodium phenylbutyrate in ALS," Amyotrophic Lateral Sclerosis, 10(2):99-106, Apr. 2009.

Duan W-M et al.: "Tauroursodeoxycholic acid improves the survival and function of nigral transplants in a rat model of Parkinson's disease", Cell Transplantation, Jan. 1, 2002, 11(3):195-205.

Dupuis et al.,"A Randomized, Double Blind, Placebo-Controlled Trial of Pioglitazone in Combination with Riluzole in Amyotrophic Lateral Sclerosis," PLoS ONE, 7(6):e37885.

Eckert et al., "Mitochondrial dysfunction—the beginning of the end in Alzheimer's disease? Separate and synergistic modes of tan and amyloid-β toxicity," Alzheimer's Res Therapy, 2011, 3:15, 11 pages.

Elia AE et al.: "Tanroursodeoxycholic acid in the treatment of patients with amyotrophic lateral sclerosis", Amyotrophic Lateral Sclerosis, Prof. Martin Maurer (Ed.), ISBN: 978-953-307-806-9, InTech, Jan. 20, 2012.

Engin et al., "Restoring endoplasmic reticulum function by chemical chaperones: an emerging therapeutic approach for metabolic diseases", Diabetes, Obesity and Metabolism, 2010, vol. 12, No. (Suppl. 2), pp. 108-115.

EP European Search Report in European Application No. 14775675.3, dated Nov. 7, 2016, 12 pages.

Franck et al., "Hepatitis C Virus NS2 Protein is Phospbosylated by the Protein Kinase CK2 and Targeted for Degradation to the Proteasome," J Virol., Mar. 2005, 79(5):2700-2708.

Freeman et al., "The influence of roller compaction processing variables on the rheological properties of granules," Asian Journal of Pharmaceutical Sciences, Aug. 1, 2016, 11(4):516-27.

Friedlich and Butcher, "Peer Commentary: Involvement of Free Oxygen Radicals in β-Amyloidosis: An Hypothesis," Neurobiol of Aging, 1994, 15(4):443-445.

Geula et al., "Aging renders the brain vulnerable to amyloid β-protein neurotoxicity," Nature Med., Jul. 1998, 4(7):827-831.

Gibson and Shi, "A Mitocentric View of Alzheimer's Disease Suggests Multi-Faceted Treatments," J Alzheimer's Dis., 2010, 20(2):S591-S607 (Author Manuscript).

Goh et al., "Phenylbutyrate Attenuates the Expression of Bcl-XL, DNA-PK, Caveolin-1, and VEGF in Prostate Cancer Cells," Neoplasia, 2001, 3(4):331-338.

Gordon et al., "Progression in ALS is not linear but is curvilinear," J Neurol, 2010, 257:1713-1717.

Grace Davidson Discovery Sciences, "Syloid 244 FP Silica Pharmaceutical Excipients, Solving Flow and Caking Challenges," <discoverysciences.com>, Aug. 2017, 3 pages.

Grace Davidson Discovery Sciences, "Syloid 244 FP Silica, Silica Excipient for Pharmaceutical Applications," <discoverysciences.com>, Apr. 2009, 2 pages.

Grace Davidson Discovery Sciences, "Syloid Silicas Pharmaceutical Excipients, Multifunctional Excipients for the Pharmaceutical Industry," <discoverysciences.com>, Sep. 2015, 4 pages.

Havashi and Sugiyama, "4-Phenylbutyrate Enhances the Cell Surface Expression and the Transport Capacity of Wild-Type and Mutated Bile Salt Export Pumps," Hepatol., 2007, 45:1506-1516.

Hayashi and Sugiyama, "Short-Chain Ubiquitination is Associated with the Degradation Rate of a Cell-Surface-Resident Bile Salt Export Pump (BSEP/ABCB11)," Mol Pharmacol., 2009, 75:143-150.

Ho et al., "Endoplasmic Reticulum Stress Induces Tau Pathology and Forms a Vicious Cycle: Implication in Alzheimer's Disease Pathogenesis," J Alzheimer's Dis., 2012, 28:839-854.

Hoozemans et al., "The Unfolded Protein Response is Activated in Pretangle Neurons in Alzheimer's Disease Hippocampus," Am J Pathol., Apr. 2009, 174(4):1241-1251.

Huang and Jiang, "Accumulated Amyloid-β Peptide and Hyperphosphorylated Tau Protein: Relationship and Links in Alzheimer's Disease," J Alzheimer's Dis., 2009, 16:15-27.

Inagi, "Endoplasmic Reticulum: The Master Regulator of Stress Responses in Glomerular Diseases," Intechopen, 2011, 21 pages.

JP Japanese Patent Application No. 2016-505464, First Office Action dated Oct. 3, 2017 and translation, 6 pages.

JP Office Action in Japanese Appln. No. 2019-040563, dated Jan. 21, 2020, 10 pages (with English translation).

Keene, CD et al.: "Tauroursodeoxycholic acid, a bile acid is neuroprotective in a transgenic animal model of Huntington's disease", PNAS, vol. 99, No. 16, Aug. 6, 2002, pp. 10671-10676.

Kitamoto et al., "Amyloid Plaques in Creutzfeldt-Jakob Disease Stain with Prion Protein Antibodies," Ann Neurol., 1986, 20:204-208.

KR Office Action in Korean Appln. No. 10-2015-7030684, dated Apr. 7, 2020, 8 pages (with English translation).

Leigh et al., "Amvotrophic lateral sclerosis: a consensus viewpoint on designing and implementing a clinical trial," ALS and other motor neuron disorders, 2004, 5:84-98.

Lindholm et al., "ER stress and neurodegenerative diseases," Cell Death Differentiation, 2006, 13:385-392.

Linger et al., "ROCK-ALS: Protocol for a Randomized, Placebo-controlled, Double-Blind Phase IIa Trial of Safety, Tolerability and Efficacy of the Rho Kinase (ROC Inhibitor Fasudil in Amyotrophic Lateral Sclerosis," Frontiers in Neurology, 2019, 10(293):1-11.

Liu et al., "The peroxisome proliferator phenylbutyric acid (PBA) protects astrocytes from ts1 MoMuLV-induced oxidative cell death," Journal of Neurovirology, Jan. 2002, 8(4): 318-325.

Liu et al., "The peroxisome proliferator phenylbutyric acid (PBA) protects astrocytes from ts1 MoMuLV-induced oxidative cell death", Journal of NeuroVirology, 8:318-325, 2002.

(56) References Cited

OTHER PUBLICATIONS

Marlatt et al., "Alzheimer's Disease: Cerebrovascular Dysfunction, Oxidative Stress, an Advanced Clinical Therapies," J Alzheimers Dis., 2009, 15(2):199-2010.
Marzioni et al., "Ca2+-Dependent Cytoprotective Effects of Ursodeoxvcholic and Tauroursodeoxvcholic Acid on the Biliary Epithelium in a Rat Model of Cholestasis and Loss of Bile Ducts," Am J Pathol., Feb. 2006, 168(2):398-409.
Material Safety Data Sheet, "Sodium Phenylbutyrate: sc-200652," May 2010, 3 pages.
Maurer M: "Amyotrophic Lateral Sclerosis: An Introduction to Treatment and Trials", Amyotrophic Lateral Sclerosis, Prof. Martin Maurer (Ed.), ISBN: 978-953-307-806-9, InTech, Jan. 20, 2012.
Mehta et al., "The dynamics of sand," Reports on Progress in Physics, Apr. 1994, 57(4):383-416.
Miki et al., "Endoplasmic reticulum stress in diabetic hearts abolishes erythropoietin-induced myocardial protection by impairment of phospho-glycogen synthase kinase-3β-mediated suppression of mitochondrial permeability transition", Diabetes, 2009, vol. 58, pp. 2863-2872.
Min J-H et al.: "Oral solubilized Ursodeoxychylic acid therapy in Amyotrophic Lateral Sclerosis: A randomized cross-over trial", The Journal of Korean Medical Science, vol. 27, No. 2, Jan. 27, 2012.
Mosbah et al., "Endoplasmic reticulum stress inhibition protects steatotic and non-steatotic livers in partial hepatectomy under ischemia-reperfusion," Cell Death Dis., 2010, 12 pages.
Muhammad et al., "Reactive Oxygen Species in Diabetes-induced Vascular Damage, Stroke, and Alzheimer's Disease," J Alzheimer's Dis., 2009, 16:775-785.
Niederwolfsgruber et al., "The Production of the Alzheimer Amyloid Precursor Protein (APP) in Extraneuronal Tissue Does Not Increase in Old Age," J Gerontol: Biol Sci., 1998, 53A(3):B186-B190.
Nunes et al., "TUDCA, a Bile Acid, Attenuates Amyloid Precursor Protein Processing and Amyloid-β Deposition in APP/PSI Mice," Mol Neurobiol., 2012, 15 pages.
Parrv GJ et al.: "Safety, tolerability, and cerebrospinal fluid penetration of Ursodeoxycholic Acid in patients with Amyotrophic Lateral Sclerosis", Clinical Nenropharmacology, Jan./Feb. 2010, 33(1):17-21.
PCT International Preliminary Report on Patentability in International Application No. PCT/US2014/018040, dated Sep. 29, 2015, received Oct. 8, 2015, 8 pages.
PCT International Search Report and Written Opinion dated Jun. 24, 2014 for International Appln. No. PCT/US2014/018040, 10 pgs.
Pogocki, "Alzheimer's β-amyloid peptide as a source of neurotoxic free radicals: the role of structural effects," Acta Neurobiol Exp., 2003, 63:131-145.
Prescott et al., "On powder flowability," Pharmaceutical Technology, Oct. 2000, 24(10):60-85.
Qi et al., "Sodium 4-Phenylbutyrate Protects against Cerebral Ischemic Injury," Mol Pharmacol., 2004, 66:899-908.
Reisberg et al., "Memantine in Moderate-to-Severe Alzheimer's Disease," N Engl J Med., 2003, 348:1333-41.
Riley et al., "Effect of particle size distribution on the friction in a powder mass," International Journal of Powder Metallurgy, 1970, (6) 17-22.
Rodrigues et al., "Amyloid β-Peptide Disrupts Mitochondrial Membrane Lipid and Protein Structure: Protective Role of Tauroursodeoxycholate," Biochem Biophys Res Comm., 2001, 281:468-474.
Roy and Kolattukudy, "Monocyte chemotactic protein-induced protein (MCPIP) promotes inflammatory angiogenesis via sequential induction of oxidative stress, endoplasmic reticulum stress and autophagy," Cellular Signalling, 2012, 24:2123-2131.
Rubio-Perez and Morillas-Ruiz, "A Review: Inflammatory Process in Alzheimer's Disease, Role of Cytokines," Scientific World J., 2012, 15 pages.
Sharma et al., "Flavouring agents in pharmaceutical formulations," Ancient Science of Life, Jul. 1988, 8(1):38.
Sharma et al., "Bile acid toxicity structure-activity relationships: Correlations between cell viability and liophilicity in a panel of new and known bile acids using an oesophageal cell line (HET-1A)," Bioorganic & Medicinal Chemistry, Sep. 2010, 18(18): 6886-6895.
Spuch et al., "New Insights in the Amyloid-Beta Interaction with Mitochondria," J Aging Res., 2012, 9 pages.
Steele and Glazier, "Is donepezil effective for treating Alzheimer's disease," CA Family Physician, Apr. 1999, 45:917-919.
Suh and Checler. "Amyloid Precursor Protein, Presenilins, and α-Synuclein: Molecular Pathogenesis and Pharmacological Applications in Alzheimer's Disease," Pharmacol Rev., 2002, 54:469-525.
Sung and Waxman, "Combination of Cytotoxic-Differentiation Therapy with 5-Fluorouracil and Phenylbutyrate in Patients with Advanced Colorectal Cancer," Anticancer Res., 2007, 27:995-1002.
Sung JJ et al.: "Tauroursodeoxycholic acid (TUDCA), a bile acid, inhibits GSNO-induced apoptosis by modulating reactive oxygen species (ROS) production in motor neuronal cells expressing mutant Cu/Zn superoxide dismutase (SOD1)", THEME 4 In vitro Experimental Models, Jul. 10, 2009, 6:sup1, p. 81, pp. 109-110.
Szweda et al., "Aging, lipofuscin formation, and free radical-mediated inhibition of cellular proteolytic systems," Ageing Res Rev., 2003, 2:383-405.
Taub, K: "TUDCA: Tauroursodeoxycholic Acid", Stanford.edu, Nov. 14, 2004, 3 pages.
Tuppo et al., "Free radical oxidative damage and Alzheimer's disease," JAOA, 2001, 101(12):S11-S15.
Vrotsos et al., "MCP-1 involvement in glial differentiation of neuroprogenitor cells through APP signaling," Brain Res Bulletin, 2009, 79:97-103.
Watson et al., "Solution Structure of Methionine-Oxidized Amyloid β-Peptide (1-40). Does Oxidation Affect Conformational Switching?" Biochem., 1998, 37:12700-12706.
Wiley et al., "Phenylbutyric Acid Rescues Endoplasmic Reticulum Stress-Induced Suppression of APP Proteolysis and Prevents Apoptosis in Neuronal Cells," PLoS One, Feb. 2010, 5(2):e9135, 17 pages.
Younce and Kolattukudy, "MCP-1 Induced Protein Promotes Adipogenesis via Oxidative Stress, Endoplasmic Reticulum Stress and Autophagy," Cell Physiol Biochem., 2012, 30:307-320.
Zhang et al., "Selective, potent blockade of the IRE1 and ATF6 pathways by 4-phenylbuyric acid analogues," British Journal of Pharmacology, Oct. 2013, 170(4): 822-834.
Berthod et al., "In vivo and in vitro models to study amyotrophic lateral sclerosis," Amyotrophic Lateral Sclerosis, Jan. 20, 2012, 81.
Bhandary et al., "An involvement of oxidative stress in endoplasmic reticulum stress and its associated diseases," International Journal of Molecular Sciences, Jan. 2013, 14(1):434-56.
Birks, "Donepezil for dementia due to Alzheimer's disease (Review)," 2009, 75 pages.
CA Office Action in Canadian Appln. No. 2,908,683, dated Oct. 22, 2020, 4 pages.
Carducci et al., "Phenylbutyrate Induces Apoptosis in Human Prostate Cancer and is More Potent Than Phenylacetate," Clin Canc Res., Feb. 1996, 2:379-387.
Carri et al., "Targets in ALS: designing multidrug therapies," Trends in Pharmacological Sciences, May 1, 2006, 27(5):267-73.
Clerc et al., "A look into the future of ALS research," Drug Discovery Today, Jun. 1, 2016, 21(6):939-49.
CN Office Action in Chinese Appln. No. 2019101142905, dated May 8, 2021, 18 pages (with English translation).
Del Signore et al., "Combined riluzole and sodium phenylbutyrate therapy in transgenic amyotrophic lateral sclerosis mice," Amyotrophic Lateral Sclerosis, Jan. 1, 2009, 10(2):85-94.
EP European Search Report in European Application No. 20169399.1, dated Nov. 6, 2020, 12 pages.
EP Notices of Opposition in European Appln. No. 14775675.3, dated Feb. 2, 2021, 29 pages.
Iannitti et al., "Clinical and experimental applications of sodium phenylbutyrate," Drugs in R&D, Sep. 2011, 11(3):227-49.
JP Office Action in Japanese Application No. 2016-505464, dated Feb. 27, 2018, 5 pages (with English translation).

(56) References Cited

OTHER PUBLICATIONS

JP Office Action in Japanese Application No. 2016-505464, dated Oct. 30, 2018, 6 pages (with English translation).
KR Office Action in Korean Appln. No. 10-2021-7005747 dated May 6, 2021, 7 pages (with English translation).
Reagan-Shaw et al., "Dose translation from animal to human studies revisited," FASEB J., 2007, 22:659-661.
Rodrigues et al., "Tanroursodeoxycholic acid prevents Bax-induced membrane perturbation and cytochrome C release in isolated mitochondria," Biochemistry, Mar. 18, 2003, 42(10):3070-80.
Rodrigues et al., "The therapeutic effects of ursodeoxycholic acid as an anti-apoptotic agent," Expert Opinion on Investigational Drugs, Jul. 1, 2001, 10(7):1243-53.
Roy et al., "Sodium phenylbutyrate controls neuroinflammatory and antioxidant activities and protects dopaminergic neurons in mouse models of Parkinson's disease," PloS one, Jun. 18, 2012, 7(6):e38113, 18 pages.
Ryu et al., "Sodium phenylbutyrate prolongs survival and regulates expression of anti-apoptotic genes in transgenic amyotrophic lateral sclerosis mice," Journal of Neurochemistry, Jun. 2005, 93(5):1087-98.
Schnabel, "Neuroscience: standard model. Nature News," Aug. 6, 2008, 454(7205):682-5.
Tallarida et al., "Quantitative methods for assessing drug synergism," Genes & Cancer, Nov. 2011, 2(11):1003-8.
Whittemore et al., "A detailed analysis of hydrogen D6 peroxide-induced cell death in primary neuronal culture," Neuroscience, Aug. 1995, 67 (4): 921-32.
Zhai et al., "Free radical-operated proteotoxic stress in macrophages primed with lipopolysaccharide," Free Radical Biol Med., 2012, 53:172-181.
Zhang et al., "Selective, potent blockade of the IRE 1 and ATF 6 pathways by 4-phenylbutyric acid analogues," British Journal of Pharmacology, Oct. 2013, 170(4):822-34.
Zhou et al., "Phenylbutyrate up-regulates the DJ-1 protein and protects neurons in cell culture and in animal models of Parkinson disease," Journal of Biological Chemistry, Apr. 29, 2011, 286(17):14941-51.
CN Office Action in Chinese Appln. No. 201910114290.5, dated Jan. 26, 2022, 9 pages (with English translation).
KR Office Action in Korean Appln. No. 10-2021-7005747 dated Nov. 15, 2021, 9 pages (with English translation).
JP Japanese Office Action in Japanese Appln. No. 2020-155505, dated Aug. 31, 2021, 10 pages (with English translation).
CA Office Action in Canadian Appln. No. 2,938,683, dated May 16, 2022, 4 pages.
CN Office Action in Chinese Appln. No. 201910114290.5, dated Jul. 6, 2022, 11 pages (with English translation).
Hogarth et al., "Sodium phenylbutyrate in Huntington's disease: A dose-finding study," Movement Disorders, Oct. 15, 2007, 22(13):1962-4.
JP Japanese Office Action in Japanese Appln. No. 2022-085433, dated Aug. 9, 2022, 13 pages (with English translation).
PCT International Preliminary Report on Patentability in International Appln. No. PCT/US2020/065145, dated May 17, 2022, 7 pages.
Walling, "Amyotrophic lateral sclerosis: Lou Gehrig's disease," American Family Physician, Mar. 15, 1999, 59(6), 11 pages.

* cited by examiner

| T1: Top Left | M1: Middle Left | B1: Bottom Left |
| --- | --- | --- |
| T2: Top Middle | M2: Middle Middle Left | B2: Bottom Middle |
| T3: Top Right | M3: Middle Middle Right | B3: Bottom Right |
| | M4: Middle Right | |

COMPOSITIONS OF BILE ACIDS AND PHENYLBUTYRATE COMPOUNDS

CROSS-REFERENCE TO RELATED APPLICATIONS

This application claims priority to U.S. Patent Application Ser. No. 62/948,756, filed Dec. 16, 2019 and U.S. Patent Application Ser. No. 63/030,793, filed May 27, 2020, each of which is incorporated herein by reference in its entirety.

TECHNICAL FIELD

The present disclosure generally relates to pharmaceutical compositions and methods of manufacturing the same.

BACKGROUND

The flow properties of powder and other bulk solids is an important consideration during the manufacturing of pharmaceutical compositions. In addition, particle size distribution also affects downstream processing and packaging of the pharmaceutical products. Certain active pharmaceutical ingredients have poor flowability and a need exists for improved pharmaceutical compositions with improved physical properties including improved flowability.

SUMMARY

The present disclosure relates to compositions comprising a phenylbutyrate compound and a bile acid and methods of processing the compositions disclosed herein.

In one aspect, provided herein are compositions that include: (a) about 15% to about 45% w/w of a phenylbutyrate compound; (b) about 5% to about 15% w/w of a bile acid; (c) about 8% to about 24% w/w of dextrates; (d) about 1% to about 6% w/w of sugar alcohol; and (e) about 22% to about 35% maltodextrin, where the phenylbutyrate compound and the bile acid have a ratio by weight of about 3:1. In some embodiments, the composition includes about 8% to about 12% w/w of the bile acid. In some embodiments, the bile acid is selected from the group consisting of: taurursodiol (TURSO, also known as tauroursodeoxycholic acid (TUDCA)), ursodeoxycholic acid (UDCA), chenodeoxycholic acid, cholic acid, hyodeoxycholic acid, lithocholic acid, and glycoursodeoxycholic acid. In some embodiments, the bile acid is TURSO. In some embodiments, the composition includes about 9.7% w/w of TURSO. In some embodiments, the composition include about 25% to about 35% w/w of the phenylbutyrate compound. In some embodiments, the phenylbutyrate compound is selected from the group consisting of: 4-phenylbutyric acid (4-PBA), Glycerly Tri-(4-phenylbutyrate), phenylacetic acid, 2-(4-Methoxyphenoxy) acetic acid (2-POAA-OMe), 2-(4-Nitrophenoxy) acetic acid (2-POAA-NO2), and 2-(2-Naphthyloxy) acetic acid (2-NOAA), and pharmaceutically acceptable salts thereof. In some embodiments, the phenylbutyrate compound is a pharmaceutically acceptable salt of 4-PBA. In some embodiments, the pharmaceutically acceptable salt of 4-PBA is sodium phenylbutyrate. In some embodiments, the composition includes about 29.2% w/w of sodium phenylbutyrate. In some embodiments, the composition includes about 10% to about 20% w/w of dextrates. In some embodiments, the composition includes about 15.6% w/w of dextrates. In some embodiments, the composition includes about 2% to about 5% w/w of sugar alcohol. In some embodiments, the sugar alcohol is selected from the group consisting of: sorbitol, xylitol, and mannitol. In some embodiments, the sugar alcohol is sorbitol. In some embodiments, the composition includes about 3.9% w/w of sorbitol. In some embodiments, the composition includes about 25% to about 32% w/w of maltodextrin. In some embodiments, the maltodextrin is pea maltodextrin. In some embodiments, the composition further includes sucralose. In some embodiments, the composition includes about 0.5% to about 5% w/w of sucralose. In some embodiments, the composition includes about 1% to about 3% w/w of sucralose. In some embodiments, the composition further includes one or more flavorants. In some embodiments, the composition includes about 2% to about 15% w/w of one or more flavorants. In some embodiments, the composition includes about 5% to about 10% w/w of flavorants.

In some embodiments, the composition further includes about 0.05% to about 2% w/w of porous silica. In some embodiments, the composition includes about 0.05% to about 1.5% w/w of porous silica. In some embodiments, the porous silica has a higher $H_2O$ adsorption capacity at a relative humidity of about 20% or higher as compared to that of fumed silica. In some embodiments, the porous silica has a higher $H_2O$ adsorption capacity at a relative humidity of about 90% or higher as compared to that of fumed silica. In some embodiments, the porous silica has an $H_2O$ adsorption capacity of about 5% to about 40% by weight at a relative humidity of about 50%. In some embodiments, the porous silica has an $H_2O$ adsorption capacity of about 30% to about 40% by weight at a relative humidity of about 50%. In some embodiments, the porous silica has a higher porosity at a relative humidity of about 20% or higher as compared to that of fumed silica. In some embodiments, the porous silica has a higher porosity at relative humidity of about 90% or higher as compared to that of fumed silica. In some embodiments, the porous silica has an average pore volume of about 0.1 cc/gm to about 2.0 cc/gm. In some embodiments, the porous silica has an average pore volume of about 0.2 to about 0.8 cc/gm. In some embodiments, the porous silica has a bulk density of about 100 g/L to about 600 g/L. In some embodiments, the porous silica has a bulk density of about 400 g/L to about 600 g/L.

In some embodiments, the composition further includes about 0.5% to about 5% w/w of a buffering agent. In some embodiments, the buffering agent is sodium phosphate. In some embodiments, the sodium phosphate is sodium phosphate dibasic. In some embodiments, the composition includes about 2.7% w/w of sodium phosphate dibasic. In some embodiments, the composition further includes about 0.05% to about 1% w/w of one or more lubricants. In some embodiments, the one or more lubricants are selected from the group consisting of: sodium stearyl fumarate, magnesium stearate, stearic acid, polyethylene glycol, glyceryl behenate, and hydrogenated oil. In some embodiments, the one or more lubricants is sodium stearyl fumarate. In some embodiments, the composition includes about 0.5% w/w of sodium stearyl fumarate.

In some embodiments, the composition has a Carr's index of about 25 or less. In some embodiments, the composition has a Carr's index of about 20 or less. In some embodiments, the composition has a Carr's index of about 12 or less.

In some embodiments, provided herein are compositions that include: about 29.2% w/w of sodium phenylbutyrate; about 9.7% w/w of TURSO; about 15.6% w/w of dextrates; about 3.9% w/w of sorbitol; about 1.9% w/w of sucralose; about 28.3% w/w of maltodextrin; about 7.3% w/w of flavorants; about 0.1% w/w of silicon dioxide; about 2.7% w/w of sodium phosphate; and about 0.5% w/w of sodium stearyl fumerate.

In another aspect, provided herein are methods of processing a composition, the methods include: (i) roller compacting a pre-blend composition that includes sodium phenylbutyrate and TURSO, where the sodium phenylbutyrate and the TURSO have a ratio by weight of about 3:1, to thereby form a compacted pre-blend; and (ii) granulating the compacted pre-blend to form granules having a Carr's index of about 12 or less. In some embodiments, the pre-blend composition includes about 15% to about 45% w/w of sodium phenylbutyrate and about 5% to about 15% w/w of TURSO. In some embodiments, the methods further include prior to step (i), blending a first composition that includes sodium phenylbutyrate and a second composition that includes TURSO, to form the pre-blend composition. In some embodiments, the first and second compositions are blended for an hour or less. In some embodiments, the first and second compositions are blended for 30 minutes or less. In some embodiments, the first and second compositions are blended at a speed of about 10 rpm to about 20 rpm. In some embodiments, the speed is about 15 rpm. In some embodiments, step (i) includes roller compacting the pre-blend composition by application of a compaction force of about 5 kN/cm to about 15 kN/cm. In some embodiments, the compaction force is about 8 kN/cm to about 12 kN/cm. In some embodiments, the compaction force is about 10 kN/cm.

In some embodiments of any of the methods described herein, step (i) includes roller compacting the pre-blend composition between at least two rotating rolls having a gap width of about 1 mm to about 5 mm. In some embodiments, the gap width is about 2 mm to about 3 mm. In some embodiments, step (i) includes roller compacting the pre-blend composition between at least two rotating rolls having a roll speed of about 4 rpm to about 12 rpm. step (i) includes roller compacting the pre-blend composition at a temperature of about 10° C. to about 30° C. In some embodiments, the methods include cooling the pre-blend composition to a temperature of about 12° C. to about 18° C.

In some embodiments of any of the methods described herein, step (ii) comprises granulating the compacted pre-blend using a granulation screen with a diameter of about 0.8 mm to about 2 mm. In some embodiments, the diameter is about 1.5 mm. In some embodiments, the methods include, prior to blending the first and second composition, sieving the first and second composition. In some embodiments, the granules have a bulk density of about 0.2 g/mL to about 1.0 g/mL. In some embodiments, the bulk density is about 0.5 g/mL to about 0.7 g/mL. In some embodiments, the granules have a tapped density of about 0.5 g/mL to about 1.2 g/mL. In some embodiments, the tapped density is about 0.7 g/mL to about 0.9 g/mL. In some embodiments, the granules have a Carr's index of about 10 or less. In some embodiments, the dissolution time for releasing about 75% of the TURSO in the granules is between about 0.5 to about 15 minutes. In some embodiments, the dissolution time for releasing about 75% of the TURSO in the granules is between about 0.5 to about 5 minutes. In some embodiments, the dissolution time for releasing about 75% of the sodium phenylbutyrate in the granules is between about 0.5 to about 15 minutes. In some embodiments, the dissolution time for releasing about 75% of the sodium phenylbutyrate in the granules is between about 0.5 to about 5 minutes.

In some embodiments of any of the methods described herein, the composition further includes: about 8% to about 24% w/w of dextrates; about 1% to about 6% w/w of sugar alcohol; and about 22% to about 35% w/w of maltodextrin. In some embodiments, the composition includes: about 29.2% w/w of sodium phenylbutyrate; about 9.7% w/w of TURSO; about 15.6% w/w of dextrates; about 3.9% w/w of sorbitol; about 1.9% w/w of sucralose; about 28.3% w/w of maltodextrin; about 7.3% w/w of flavorants; about 0.1% w/w of silicon dioxide; about 2.7% w/w of sodium phosphate; and about 0.5% w/w of sodium stearyl fumerate.

Unless otherwise defined, all terms of art, notations, and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DETAILED DESCRIPTION

Figure 1:
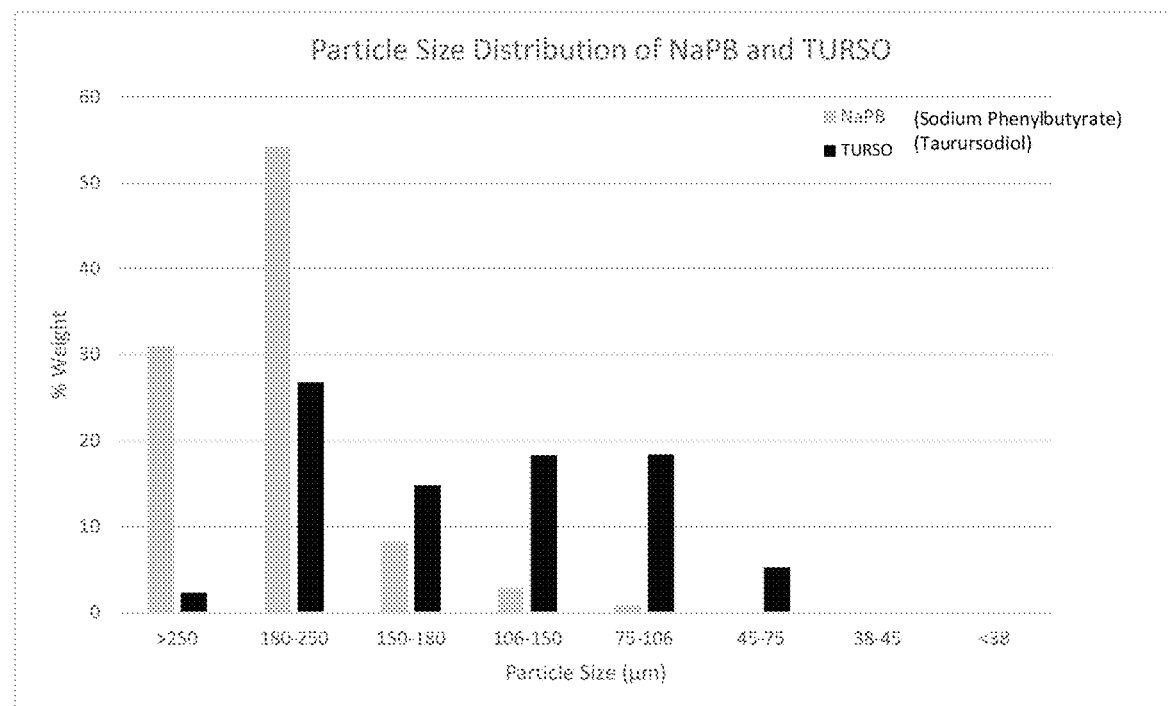
FIG. 1 shows the particle size distribution of sodium phenylbutyrate and TURSO.

Active pharmaceutical ingredients, such as bile acids and phenylbutyrate compounds can have poor flow properties, which affect, among other things, downstream processing, including mixing, scale-up, and packaging of powdered pharmaceutical products. Agglomeration of the powdered materials can also affect content uniformity and downstream processing. The present disclosure provides formulations containing bile acids and phenylbutyrate compounds and methods of manufacturing the same that demonstrate improved flow properties, uniformity, stability, and reduced agglomeration of the final granulate product. Accordingly, the present disclosure provides compositions that include (a) about 15% to about 45% w/w of a phenylbutyrate compound (e.g., any of the phenylbutyrate compounds described herein or known in the art); (b) about 5% to about 15% w/w of a bile acid (e.g., any of the bile acids described herein or known in the art); (c) about 8% to about 24% w/w of dextrates (e.g., any of the dextrates described herein or known in the art); (d) about 1% to about 6% w/w of sugar alcohol (e.g., any of the sugar alcohols described herein or known in the art); and (e) about 22% to about 35% maltodextrin, wherein the phenylbutyrate compound and the bile acid have a ratio by weight of about 3:1. The compositions of the present disclosure can have a Carr's index of about 25 or less, about 20 or less, or about 12 or less. In some embodiments of any of the compositions described herein, the composition is water soluble.

The manufacturing methods provided herein are based in part on a dry granulation process. The present inventors have discovered method of processing a composition that result in improved flow properties and stability as compared to the active pharmaceutical compositions alone. Accordingly, provided herein are methods of processing a composition, the methods include: (i) roller compacting a pre-blend composition comprising sodium phenylbutyrate and TURSO, wherein the sodium phenylbutyrate and the TURSO have a ratio by weight of about 3:1, to thereby form a compacted pre-blend; and (ii) granulating the compacted pre-blend to form granules having a Carr's index of about 12 or less. The methods described herein can also include prior to step (i) blending a first composition comprising sodium phenylbutyrate and a second composition comprising TURSO, to form the pre-blend composition.

Carr's Index

In some embodiments of any of the compositions described herein, the composition has a Carr's index of about 25 or less. For example, the composition can have a Carr's index of about 21 to about 25 (e.g., about 22, 23, or 24), about 16 to about 20 (e.g., about 17, 18, or 19), about 11 to about 15 (e.g. about 12, 13, or 14), or about 10 or less (e.g., 9, 8, 7, 6, 5, 4, 3, 2, or 1). In some embodiments, the composition has a Carr's index of about 26 to about 31 (e.g., about 27, 28, 29, or 30), about 32 to about 37 (e.g., about 32, 33, 34, 35, or 36), or above about 38.

The Carr's index (or Carr's compressibility index) of a composition can indicate the compressibility (or the propensity of a composition to be compressed) and flowability of a material. In some cases, Carr's index is associated with the bulk and tapped density of a material. Bulk density is a property of materials such as powders and granules, and can be measured by dividing the mass of the particles in the material by the total volume occupied. The total volume can include particle volume, inter-particle void volume, and/or internal pore volume. For a powder material, bulk density can depend on both the density of the particles and the spatial arrangement of the particles in the powder. Tapped density is typically an increased bulk density attained after a specified compaction process, such as mechanically tapping or vibrating a container containing the material.

Bulk density and tapped density of a composition containing powders or granules can be measured using methods known in the art. For example, the bulk density of a powder can be the ratio between the mass and volume of an untapped sample. The bulk density of a powder can also be determined by measuring the volume of a known weight of a powder sample that may have been passed through a sieve, into a container (e.g., a graduated cylinder), or by measuring the mass of a known volume of powder that has been passed through a volumeter into a container. Tapped density can be obtained, for example, by mechanically tapping a container (e.g., a graduated measuring cylinder or vessel) containing the sample. The Carr's index of a material can be calculated based on the bulk and tapped densities, for example, according to the formula $C = 100 \, (1 - pB/pT)$ (C stands for Carr's index, pB stands for bulk density, and pT stands for tapped density). Additional methods of determining the Carr's index of a material can be found at, e.g., ASTM-D6393, Standard test method for bulk solids characterization by Carr indices, J. ASTM Int. 04.09 (2014); and R. E. Riley, H. H. Hausner, Effect of particle size distribution on the friction in a powder mass, Int. J. Powder Metall. 6 (1970) 17-22.

Carr's index can indicate the flowability of a material. For example, a higher Carr's index (a larger difference in bulk versus tapped densities) can be associated with lower flowability. Hausner ratio, or the tapped-to-bulk density ratio, which can be expressed as $H = pT/pB$, can also be associated with the flowability of a material.

Additional flow indices are also contemplated herein for measuring the flowability of a material, such as the angle of repose. The angle of repose of a granular material can be represented by the steepest slope of the unconfined material, measured from the horizontal plane on which the material can be heaped without collapsing (See, e.g., Mehta et al. Prog. Phys. 57 (1994) 383-416). Exemplary methods of measuring the angle of repose of a material can be found at, e.g. Beakawi et al., Powder Technology 330 (2018) 397-417. For powders, which can be defined as small-sized granular materials subject to cohesion and suspension in a gas, the definition of the angle of repose can be associated with the Hausner ratio (See, e.g. Beddow Part. Part. Syst. Charact. 12 (4): 213, 1995), and the powders can flow at angles greater than the angle of repose. The angle of repose can also indicate the cohesiveness of the granular material, referring to the Carr classification of flowability shown below.

| Description | Repose Angle |
|---|---|
| Very free-flowing | <30° |
| Free flowing | 30-38° |
| Fair to passable flow | 38-45° |
| Cohesive | 45-55° |
| Very cohesive (non-flowing) | >55° |

Bile Acids

The present disclosure provides compositions that include about 5% to about 15% w/w (e.g., about 6% to about 14%, about 7% to about 13%, about 8% to about 12%, about 8% to about 11%, about 9% to about 10%, or about 9.7% w/w) of a bile acid. Bile acids as described herein can include naturally occurring surfactants having a nucleus derived from cholanic acid substituted with a 3α-hydroxyl group, and optionally with other hydroxyl groups, typically at the C6, C7 or C12 position of the sterol nucleus. Suitable bile acids include but are not limited to, Taurursodiol (TURSO), ursodeoxycholic acid (UDCA), chenodeoxycholic acid (also referred to as "chenodiol" or "chenic acid"), cholic acid, hyodeoxycholic acid, deoxycholic acid, 7-oxolithocholic acid, lithocholic acid, iododeoxycholic acid, iocholic acid, taurochenodeoxycholic acid, taurodeoxycholic acid, glycoursodeoxycholic acid, taurocholic acid, glycocholic acid, cholic acid, or an analog, derivative, or prodrug thereof. In some embodiments, the bile acids are hydrophilic bile acids, including but not limited to, TURSO, UDCA, chenodeoxycholic acid, cholic acid, hyodeoxycholic acid, lithocholic acid, and glycoursodeoxycholic acid. Pharmaceutically acceptable salts or solvates of any of the bile acids described herein are also contemplated. Bile acid derivatives are also contemplated, which include but are not limited to derivatives formed at the hydroxyl and carboxylic acid groups of the bile acid with other functional groups such as halogens and amino groups. TURSO and Taursodeoxycholic acid (TUDCA) are used interchangeably herein.

The bile acid described herein can be TURSO as shown in formula I (with labeled carbons to assist in understanding where substitutions may be made).

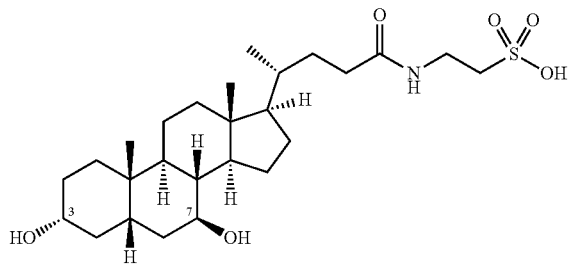

I

The compositions described herein can include about 5% to about 15% w/w (e.g., any of the subranges of this range described herein) of TURSO. In some embodiments, the composition includes about 9.7% of TURSO. The TURSO of any of the compositions described herein can have a Carr's index of about 22 to about 26 (e.g., about 23, 24, or 25).

The bile acid described herein can be UDCA as shown in formula II (with labeled carbons to assist in understanding where substitutions may be made).

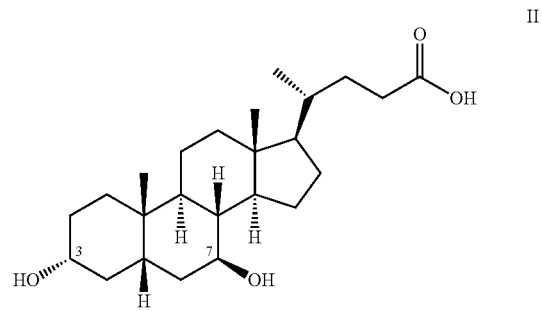

II

Physiologically related bile acid derivatives, for example, compounds having any combination of substitutions of hydrogen at position 3 or 7 and/or a shift in the stereochemistry of the hydroxyl group at positions 3 or 7 in the formula of TURSO or UDCA are suitable for use in the present composition.

Amino acid conjugates of any of the bile acids described herein or known in the art, or a pharmaceutically acceptable salt thereof are also suitable for the presently described compositions. The amino acid in the conjugate can be, but are not limited to, taurine, glycine, glutamine, asparagine, methionine, or carbocysteine. For example, encompassed by the present disclosure is a compound of formula III:

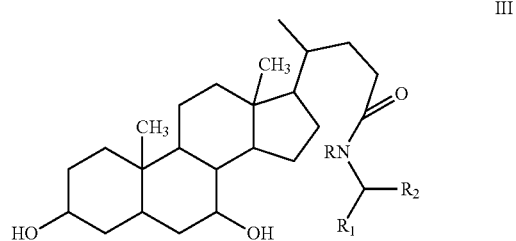

III wherein R is —H or $C_1$-$C_4$ alkyl; $R_1$ is —$CH_2$—$SO_3R_3$ and $R_2$ is —H; or $R_1$ is —COOH and $R_2$ is —$CH_2$—$CH_2$—$CONH_2$, —$CH_2$—$CONH_2$, —$CH_2$—$CH_2$—$SCH_3$, or —$CH_2$—S—$CH_2$—COOH; and $R_3$ is —H or the residue of a basic amino acid, or a pharmaceutically acceptable salt, analog, derivative, prodrug thereof, or a mixture thereof.

Phenylbutyrate Compounds

The present disclosure provides compositions that include about 15% to about 45% w/w (e.g., about 20% to about 40%, about 25% to about 35%, about 28% to about 32%, or about 29% to about 30%, e.g., about 29.2% w/w) of a phenylbutyrate compound. Phenylbutyrate compounds described herein encompass phenylbutyrate (a low molecular weight aromatic carboxylic acid) as a free acid (4-phenylbutyrate (4-PBA), 4-phenylbutyric acid, or phenylbutyric acid), and pharmaceutically acceptable salts, co-crystal, polymorph, hydrate, solvates, conjugates, derivatives or prodrugs thereof. Phenylbutyrate compounds described herein also encompass analogs of 4-PBA, including but not limited to, Glycerly Tri-(4-phenylbutyrate), phenylacetic acid (which is the active metabolite of 4-PBA), 2-(4-Methoxyphenoxy) acetic acid (2-POAA-OMe), 2-(4-Nitrophenoxy) acetic acid (2-POAA-NO2), and 2-(2-Naphthyloxy) acetic acid (2-NOAA), and their pharmaceutically acceptable salts. The structures of the 4-PBA analogs can be found at e.g., Zhang et al., Br J Pharmacol 2013 October; 170(4): 822-834. Phenylbutyrate compounds also encompass physiologically related 4-PBA species, such as but not limited to those having any substitutions for Hydrogens with Deuterium in the structure of 4-PBA. Physiologically acceptable salts of 4-PBA, include, for example sodium, potassium, magnesium and calcium salts.

In some embodiments, the present disclosure provides compositions comprising about 15% to about 45% w/w (e.g., any of the subranges of this range described herein) of sodium phenylbutyrate. In some embodiments, the composition includes about 29.2% of sodium phenylbutyrate. The sodium phenylbutyrate of any of the compositions described herein can have a Carr's index of about 35 or more (e.g., about 36, 37, 38, 39, or 40 or more). Sodium phenylbutyrate has the following structure:

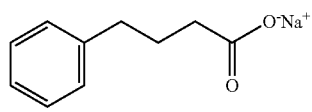

IV

In some instances, the combination of a bile acid (e.g., TURSO) and a phenylbutyrate compound (e.g. sodium phenylbutyrate) has synergistic efficacy when administered to a subject for treating one or more symptoms associated with neurodegenerative diseases. Exemplary neurodegenerative diseases include, but are not limited to, amyotrophic lateral sclerosis (ALS), Alzheimer's disease, Multiple Sclerosis (MS), Parkinson's disease, Huntington's disease, stroke, Pick's Disease, Multi-Infarct Dementia, Creutzfeldt-Jakob's Disease, Dementia with Lewy bodies, Mixed dementia and Frontotemporal dementia. The combination of a bile acid and a phenylbutyrate compound can, for example, induce a mathematically synergistic increase in neuronal viability in a strong oxidative insult model ($H_2O_2$-mediated toxicity) by linear modeling. Such combination therapies are disclosed in U.S. Pat. Nos. 9,872,865 and 10,251,896.

In some embodiments, the phenylbutyrate compound and the bile acid in the compositions provided herein have a ratio by weight of between about 1:1 to about 4:1 (e.g., 2:1 or 3:1). In some embodiments, the phenylbutyrate compound and the bile acid in the compositions provided herein have a ratio by weight of between about 3:1.

Dextrates

Some embodiments of any of the compositions described herein include about 8% to about 24% w/w (e.g., about 9% to about 23%, about 10% to about 22%, about 10% to about 20%, about 11% to about 21%, about 12% to about 20%, about 13% to about 19%, about 14% to about 18%, about 14% to about 17%, about 15% to about 16%, or about 15.6% w/w) of dextrates. Both anhydrous and hydrated dextrates are contemplated herein. The dextrates of the present disclosure can include a mixture of saccharides developed from controlled enzymatic hydrolysis of starch. Some embodiments of any of the compositions described herein include hydrated dextrates (e.g., NF grade, obtained from JRS Pharma, Colonial Scientific, or Quadra).

Sugar Alcohol

Some embodiments of any of the compositions described herein include about 1% to about 6% w/w (e.g., about 2% to about 5%, about 3% to about 4%, or about 3.9% w/w) of sugar alcohol. Sugar alcohols can be derived from sugars and contain one hydroxyl group (—OH) attached to each carbon atom. Both disaccharides and monosaccharides can form sugar alcohols. Sugar alcohols can be natural or produced by hydrogenation of sugars. Exemplary sugar alcohols include but are not limited to, sorbitol, xylitol, and mannitol. In some embodiments, the composition comprises about 1% to about 6% w/w (e.g., about 2% to about 5%, about 3% to about 4%, or about 3.9% w/w) of sorbitol.

Maltodextrin

Some embodiments of any of the compositions described herein include about 22% to about 35% w/w (e.g., about 22% to about 33%, about 24% to about 31%, about 25% to about 32%, about 26% to about 30%, or about 28% to about 29% w/w, e.g., about 28.3% w/w) of maltodextrin. Maltodextrin can form a flexible helix enabling the entrapment of the active ingredients (e.g., any of the phenylbutyrate compounds and bile acids described herein) when solubilized into solution, thereby masking the taste of the active ingredients. Maltodextrin produced from any suitable sources are contemplated herein, including but not limited to, pea, rice, tapioca, corn, and potato. In some embodiments, the maltodextrin is pea maltodextrin. In some embodiments, the composition includes about 28.3% w/w of pea maltodextrin. For example, pea maltodextrin obtained from Roquette (KLEPTOSE® LINECAPS) can be used.

Sucralose

Some embodiments of any of the compositions described herein further include sucralose. In some embodiments, the compositions described herein include about 0.5% to about 5% w/w (e.g., about 1% to about 4%, about 1% to about 3%, or about 1% to about 2%, e.g., about 1.9% w/w) of sucralose. Other sugar substitutes contemplated herein include but are not limited to aspartame, neotame, acesulfame potassium, saccharin, and advantame.

Flavorants

Some embodiments of any of the compositions described herein further include one or more flavorants. In some embodiments, the compositions described herein include about 2% to about 15% w/w (e.g., about 3% to about 13%, about 3% to about 12%, about 4% to about 9%, about 5% to about 10%, or about 5% to about 8%, e.g., about 7.3% w/w) of flavorants. Flavorants can include substances that give another substance flavor, or alter the characteristics of a composition by affecting its taste. Flavorants can be used to mask unpleasant tastes without affecting physical and chemical stability, and can be selected based on the taste of the drug to be incorporated. Suitable flavorants include but are not limited to natural flavoring substances, artificial flavoring substances, and imitation flavors. In some embodiments, blends of flavorants are used. For example, the compositions described herein can include two or more (e.g., two, three, four, five or more) flavorants. The flavorants described herein can be soluble and stable in water. Selection of suitable flavorants can be based on taste testing. For example, multiple different flavorants can be added to a composition separately, which are subjected to taste testing. Exemplary flavorants include any fruit flavor powder (e.g., peach, strawberry, mango, orange, apple, grape, raspberry, cherry or mixed berry flavor powder). In some embodiments, any of the compositions described herein includes about 0.5% to about 1.5% w/w (e.g., about 1% w/w) of a mixed berry flavor powder. In some embodiments, any of the compositions described herein includes about 5% to about 7% w/w (e.g., about 6.3% w/w) of a masking flavor. Suitable masking flavors can be obtained from e.g., Firmenich.

Silica

Some embodiments of any of the compositions provided herein further include silicon dioxide (or silica). Addition of silica to the composition can prevent or reduce agglomeration of the components of the composition. Silica can serve as an anti-caking agent, adsorbent, disintegrant, or glidant. In some embodiments, the compositions described herein include about 0.05% to about 2% w/w (e.g., about 0.05% to about 1.5%, about 0.07% to about 1.2%, or about 0.08% to about 0.1%, e.g., 0.09% w/w) porous silica. Porous silica can, for example, have a higher $H_2O$ absorption capacity and/or a higher porosity as compared to fumed silica, at a relative humidity of about 20% or higher (e.g., about 25%, 30%, 35%, 40%, 45%, 50%, 55%, 60%, 65%, 70%, 75%, 80%, 85%, 90%, or 95% or higher). In some embodiments, the porous silica have an $H_2O$ absorption capacity of about 5% to about 40% (e.g. about 20% to about 40%, or about 30% to about 40%) by weight at a relative humidity of about 50%. The porous silica can have a higher porosity at a relative humidity of about 20% or higher (e.g., about 30%, 40%, 50%, 60%, 70%, 80%, 90% or higher) as compared to that of fumed silica. In some embodiments, the porous silica have an average particle size of about 2 μm to about 10 μm (e.g. about 3 μm to about 9 μm, about 4 μm to about 8 μm, about 5 μm to about 8 μm, or about 7.5 μm). In some embodiments, the porous silica have an average pore volume of about 0.1 cc/gm to about 2.0 cc/gm (e.g., about 0.1 cc/gm to about 1.5 cc/gm, about 0.1 cc/gm to about 1 cc/gm, about 0.2 cc/gm to about 0.8 cc/gm, about 0.3 cc/gm to about 0.6 cc/gm, or about 0.4 cc/gm). In some embodiments, the porous silica have a bulk density of about 50 g/L to about 700 g/L (e.g. about 100 g/L to about 600 g/L, about 200 g/L to about 600 g/L, about 400 g/L to about 600 g/L, about 500 g/L to about 600 g/L, about 540 g/L to about 580 g/L, or about 560 g/L). In some embodiments, the compositions described herein include about 0.05% to about 2% w/w (e.g., any subranges of this range described herein) of Syloid® 63FP (WR Grace).

Buffering Agents and Lubricants

Some embodiments of any of the compositions described herein further include one or more buffering agents. In some embodiments, the composition includes about 0.5% to about 5% w/w (e.g., about 1% to about 4%, about 1.5% to about 3.5%, or about 2% to about 3%, e.g. about 2.7% w/w) of buffering agents. Buffering agents can include weak acid or base that maintain the acidity or pH of a composition near a chosen value after addition of another acid or base. Suitable buffering agents are known in the art. In some embodiments, the buffering agent in the composition provided herein is a phosphate, such as a sodium phosphate (e.g., sodium phosphate dibasic anhydrous). For example, the composition can include about 2.7% w/w of sodium phosphate dibasic.

Some embodiments of any of the compositions described herein further include one or more lubricants. In some embodiments, the composition includes about 0.05% to about 1% w/w (e.g., about 0.1% to about 0.9%, about 0.2% to about 0.8%, about 0.3% to about 0.7%, or about 0.4% to about 0.6%, e.g. about 0.5% w/w) of lubricants. Exemplary lubricants include, but are not limited to sodium stearyl fumarate, magnesium stearate, stearic acid, metallic stearates, talc, waxes and glycerides with high melting temperatures, colloidal silica, polyethylene glycols, alkyl sulphates, glyceryl behenate, and hydrogenated oil. Additional lubricants are known in the art. In some embodiments, the composition includes about 0.05% to about 1% w/w (e.g., any of the subranges of this range described herein) of sodium stearyl fumarate. For example, the composition can include about 0.5% w/w of sodium stearyl fumarate.

Additional suitable sweeteners or taste masking agents can also be included in the compositions described herein, such as but not limited to, xylose, ribose, glucose, mannose, galactose, fructose, dextrose, sucrose, maltose, steviol glycosides, partially hydrolyzed starch, and corn syrup solid. Water soluble artificial sweeteners are contemplated herein, such as the soluble saccharin salts (e.g., sodium or calcium saccharin salts), cyclamate salts, acesulfam potassium (acesulfame K), and the free acid form of saccharin and aspartame based sweeteners such as L-aspartyl-phenylalanine methyl ester, Alitame® or Neotame®. The amount of sweetener or taste masking agents can vary with the desired amount of sweeteners or taste masking agents selected for a particular final composition.

Pharmaceutically acceptable binders in addition to those described above are also contemplated for the compositions described herein. Examples include cellulose derivatives including microcrystalline cellulose, low-substituted hydroxypropyl cellulose (e.g. LH 22, LH 21, LH 20, LH 32, LH 31, LH30); starches, including potato starch; croscarmellose sodium (i.e. cross-linked carboxymethylcellulose sodium salt; e.g. Ac-Di-Sol®); alginic acid or alginates; insoluble polyvinylpyrrolidone (e.g. Polyvidon® CL, Polyvidon® CL-M, Kollidon® CL, Polyplasdone® XL, Polyplasdone® XL-10); sodium carboxymethyl starch (e.g. Primogel® and Explotab®).

Additional fillers, diluents or binders may be incorporated such as polyols, sucrose, sorbitol, mannitol, Erythritol®, Tagatose®, lactose (e.g., spray-dried lactose, α-lactose, β-lactose, Tabletose®, various grades of Pharmatose®, Microtose or Fast-Floc®), microcrystalline cellulose (e.g., various grades of Avicel®, such as Avicel® PH101, Avicel® PH102 or Avicel® PH105, Elcema® P100, Emcocel®, Vivacel®, Ming Tai® and Solka-Floc®), hydroxypropylcellulose, L-hydroxypropylcellulose (low-substituted) (e.g. L-HPC-CH31, L-HPC-LH11, LH 22, LH 21, LH 20, LH 32, LH 31, LH30), dextrins, maltodextrins (e.g. Lodex® 5 and Lodex® 10), starches or modified starches (including potato starch, maize starch and rice starch), sodium chloride, sodium phosphate, calcium sulfate, and calcium carbonate.

Pharmaceutical Compositions

Any of the compositions described herein can be formulated for use as or in pharmaceutical compositions. Such compositions can be formulated or adapted for administration to a subject via any route, e.g., any route approved by the Food and Drug Administration (FDA), such as but not limited to oral, parenteral, or transdermal delivery. Exemplary methods are described in the FDA's CDER Data Standards Manual, version number 004 (which is available at fda.give/cder/dsm/DRG/drg00301.html).

In some embodiments, the compositions described herein is used for treating or preventing one or more symptoms associated with a neurodegenerative disease in a subject in need thereof. Exemplary neurodegenerative diseases include, but are not limited to amyotrophic lateral sclerosis (ALS), Alzheimer's disease, Multiple Sclerosis (MS), Parkinson's disease, Huntington's disease, Pick's Disease, Multi-Infarct Dementia, Creutzfeldt-Jakob's Disease, Dementia with Lewy bodies, Mixed dementia, and frontotemporal dementia.

Any of the compositions described herein can be formulated as a pharmaceutical composition that further includes one or more additional therapeutic agents. Exemplary additional therapeutic agents include riluzole ($C_8H_5F_3N_2OS$, sold under the trade names Rilutek® and Tiglutik®), edaravone (sold under the trade names Radicava® and Radicut®), mexiletine (sold under the trade names Mexitil and NaMuscla), a combination of dextromethorphan and quinidine (Nuedexta®), anticholinergic medications, and psychiatric medications such as but not limited to antidepressants, antipsychotics, anxiolytics/hypnotics, mood stabilizers, and stimulants. Any known anticholinergic medications are contemplated herein, including but are not limited to, glycopyrrolate, scopolamine, atropine (Atropen), belladonna alkaloids, benztropine mesylate (Cogentin), clidinium, cyclopentolate (Cyclogyl), darifenacin (Enablex), dicylomine, fesoterodine (Toviaz), flavoxate (Urispas), glycopyrrolate, homatropine hydrobromide, hyoscyamine (Levsinex), ipratropium (Atrovent), orphenadrine, oxybutynin (Ditropan XL), propantheline (Pro-banthine), scopolamine, methscopolamine, solifenacin (VESIcare), tiotropium (Spiriva), tolterodine (Detrol), trihexyphenidyl, trospium, and diphenhydramine (Benadryl). Any known antidepressants are contemplated herein as additional therapeutic agents, including but not limited to selective serotonin inhibitors, serotonin-norepinephrine reuptake inhibitors, serotonin modulators and stimulators, serotonin antagonists and reuptake inhibitors, norepinephrine reuptake inhibitors, norepinephrine-dopamine reuptake inhibitors, tricyclic antidepressants, tetracyclic antidepressants, monoamine oxidase inhibitors, and NMDA receptor antagonists.

The pharmaceutical compositions described herein can further include any pharmaceutically acceptable carrier, adjuvant and/or vehicle. Pharmaceutically acceptable carrier or adjuvant refers to a carrier or adjuvant that may be administered to a patient, and which does not destroy the pharmacological activity thereof and is nontoxic when administered in doses sufficient to deliver a therapeutic amount of the active compounds. Exemplary pharmaceutically acceptable carriers include saline, solvents, dispersion media, coatings, antibacterial and antifungal agents, and isotonic and absorption delaying agents, which are compatible with pharmaceutical administration. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Any of the therapeutic compositions disclosed herein can be formulated for sale in the US, imported into the US, and/or exported from the US. The pharmaceutical compositions can be included in a container, pack, or dispenser together with instructions for administration. In some aspects, the invention provides kits that include the bile acid and phenylbutyrate compounds. The kit may also include instructions for the physician and/or patient, syringes, needles, box, bottles, vials, etc.

Dosage and Method of Administration

Pharmaceutical compositions are typically formulated to be compatible with its intended route of administration. Examples of routes of administration include parenteral, e.g., intravenous, intradermal, subcutaneous, oral (e.g., inhalation or through a feeding tube), transdermal (topical), transmucosal, and rectal administration.

Pharmaceutical compositions can be in the form of a solution or powder for inhalation and/or nasal administration. Such compositions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium.

Pharmaceutical compositions can be orally administered in any orally acceptable dosage form including, but not limited to, powders, capsules, tablets, emulsions and aqueous suspensions, dispersions and solutions. In the case of tablets for oral use, carriers which are commonly used include lactose and corn starch. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, coloring agents may be added. The solid formulation can be reconstituted in an aqueous solvent (e.g., water, saline solution) to prepare an aqueous formulation. As used herein, the term "aqueous solvent" refers to a liquid comprising at least 50% (e.g., at least 60%, 70%, 80%, 90% or at least 95%) water. In some embodiments, the aqueous solvent is water.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, any of the compositions described herein is substantially dissolved in water prior to oral administration to a subject. The compositions of the present disclosure can be administered to a subject in need thereof once a day, twice a day, or three times a day or more.

In some embodiments, the bile acid (e.g., TURSO) of the composition is administered at an amount of about 0.5 to about 5 grams (e.g., about 0.5 to about 4.5, about 0.5 to about 3.5, about 1 to about 3, e.g., about 2 grams) per day. In some embodiments, the bile acid is TURSO and is administered at an amount of about 2 grams per day, for example, one gram is administered twice a day. In some embodiments, the bile acid is administered at about 10 mg/kg to about 50 mg/kg (e.g., about 10 mg/kg to about 40 mg/kg, about 10 mg/kg to about 30 mg/kg, about 10 mg/kg to about 20 mg/kg, about 10 mg/kg to about 15 mg/kg, or about 13 mg/kg to about 15 mg/kg) of the body weight of the subject.

In some embodiments, the phenylbutyrate compound (e.g., sodium phenylbutyrate) of the composition is administered at an amount of about 0.5 to about 10 grams (e.g., about 1 to about 10, about 2 to about 9, about 3 to about 8, about 5 to about 7, e.g., about 6 grams) per day. In some embodiments, the bile acid is sodium phenylbutyrate and is administered at an amount of about 6 grams per day, for example, three grams is administered twice a day. In some embodiments, the phenylbutyrate compound is administered at about 10 mg/kg to about 400 mg/kg (e.g., about 10 mg/kg to about 300 mg/kg, about 10 mg/kg to about 200 mg/kg, about 10 mg/kg to about 100 mg/kg, about 10 mg/kg to about 80 mg/kg, about 30 mg/kg to about 80 mg/kg, or about 30 mg/kg to about 50 mg/kg) of the body weight of the subject.

In some embodiments, the composition is administered once a day or twice a day and each administration includes about 1 gram of TURSO and about 3 grams of sodium phenylbutyrate. In some embodiments, the composition is administered once a day and each administration contains about 2 grams of TURSO and about 6 grams of sodium phenylbutyrate.

The composition can be administered to a subject in need thereof for at least about six months (e.g., at least about 7, 8, 9, 10, 11, 12, 13, 14, 15, 16, 16, 18, 20, 21, 22, 23, or 24 months). In some embodiments, the composition is administered to a subject in need thereof for less than about 6 months (e.g., less than about 5, 4, 3, 2, or 1 month).

Methods of Processing

This disclosure further relates to methods of processing or manufacturing a pharmaceutical formulation based on dry granulation. Provided herein are methods of processing a composition, the methods include: (i) roller compacting a pre-blend composition comprising sodium phenylbutyrate and TURSO, wherein the sodium phenylbutyrate and the TURSO have a ratio by weight of about 3:1, to thereby form a compacted pre-blend; and (ii) granulating the compacted pre-blend to form granules having a Carr's index of about 12 or less.

The pre-blend composition can include about 15% to about 45% w/w (e.g., any of the subranges of this range described herein) of sodium phenylbutyrate and about 5% to about 15% w/w (e.g., any of the subranges of this range described herein) of TURSO.

Some embodiments of any of the methods of processing a composition described herein further include, prior to step (i), blending a first composition comprising sodium phenylbutyrate and a second composition comprising TURSO, to form the pre-blend composition.

A step of sieving the first composition comprising sodium phenylbutyrate and the second composition comprising TURSO can be performed prior to blending. Such sieving can be carried out with any conventional sieving means known to the skilled person.

The first and second compositions can be blended for about an hour or less (e.g., about 55, 50, 45, 40, 35, 30, or 25 minutes or less), and/or at a blending speed of about 10 rpm to about 20 rpm (e.g., about 12 rpm to about 18 rpm, about 14 to about 16, e.g., about 15 rpm). Blending time and blending speed can be adjusted so as to achieve an essentially homogenous admixture of components. Blending speed can either be fixed or adjusted during blending. In some embodiments, blending the first and second compositions for about 30 minutes or less (e.g., about 29, 28, 27, or 26 minutes or less, e.g., about 25 minutes or about 15 minutes) result in less particle attrition as compared to blending the composition for more than 30 minutes and is therefore more desired. Suitable blending equipment and parameters are known in the art. For example, any apparatus typically employed in the pharmaceutical industry for uniformly admixing two or more components, including V-shaped blenders, double-cone blenders, bin (container) blenders, and rotary drum blenders can be used. Blender volume can be 50 L, 100 L, 200 L, 250 L or greater. Before, during, or after blending, the composition may also be subjected to milling under suitable milling speed. Suitable milling equipment and parameters are known in the art.

The term "roller compacting" refers to a process in which powders are forced between two counter rotating rolls and pressed into a solid compact or ribbon. Roller compaction can be carried out with any suitable roller compactor known to the skilled person. For example, a MACRO-PACTOR® or a MINI-PACTOR® from Gerteis can be used. The step of granulating the solid compact or ribbon into granules involves milling/sieving the compact or ribbon into desired granulate size, and can be carried out by a roller compactor that integrates the roller compacting and milling functions, or can be carried out on a separate equipment. "Granulating" and "milling" are used interchangeably herein and can refer to a process of breaking solid materials into smaller pieces, for example, by grinding, crushing, or cutting.

A roller compactor can generally consist of three major units: a feeding system, which conveys the powder to the compaction area between the rolls; a compaction unit, where powder is compacted between two counter rotating rolls to a ribbon by applying a force; and a size reduction unit, for milling the ribbons to the desired particle size.

Several operational parameters can be adjusted/controlled to modify the product granulate, including the compaction force, the gap width and the granulation screen size. The compaction force can be expressed in kN/cm, which refers to the force per cm roll width. The gap width refers to the width of the gap between the two of the rotating rollers. As the gap width increases, the constant force applied by the roller has to be transmitted through a thicker ribbon of powder and thus the ribbon may have a lower strength and will likely result in smaller, weaker granules following the milling process. Additional descriptions of the roller compaction processing variables can be found in e.g. Freeman et al. Asian Journal of Pharmaceutical Sciences 11:516-527, 2016.

The compaction force used in step (i) can be about 5 kN/cm to about 15 kN/cm (e.g., about 7 kN/cm to about 13 kN/cm, about 8 kN/cm to about 12 kN/cm, or about 9 kN/cm to about 11 kN/cm, e.g., about 10 kN/cm). In some embodiments of any of the methods described herein, step (i) can include roller compacting the pre-blend composition between at least two rotating rolls having a gap width of about 1 mm to about 5 mm, about 2 mm to about 4 mm, or about 2 mm to about 3 mm. The rotating rolls can have a roll speed of about 4 rpm to about 12 rpm (e.g. about 5, 6, 7, 8, 9, 10, or 11 rpm). Roller compaction can be performed at a temperature that prevents melting or agglomeration of the composition. For example, the pre-blend composition can be roller compacted at a temperature of about 10° C. to about 30° C. (e.g., about 12° C. to about 30° C., about 12° C. to about 20° C., or about 12° C. to about 18° C., about 15° C. to about 25° C., about 20° C. to about 30° C., or about 24° C. to about 29° C.). A cooling unit set to a temperature of about 10° C. to about 20° C. (e.g., about 12° C. to about 18° C., or about 13° C. to about 17° C.) can be added to the roller compactor for this purpose. The rotating rolls can, for example, have a temperature of about 10° C. to about 30° C. (e.g., any of the subranges within this range described herein).

In some embodiments of any of the methods described herein, step (ii) includes granulating the compacted pre-blend to form granules. A granulation screen with a diameter of about 0.8 mm to about 2 mm (e.g., about 1 mm to about 1.8 mm, about 1.2 mm to about 1.7 mm, about 1.4 mm to about 1.6 mm or e.g. about 1.5 mm) can be used. The methods can also include a step of sieving the granules by at least one suitable mesh size.

The methods described herein can further include a step of final blending, following step (ii), which includes blending the granules for 10 minutes or less, or 5 minutes or less.

The granules prepared by the present methods can have a bulk density of about 0.2 g/mL to about 1.0 g/mL (e.g., about 0.2 g/mL to about 0.9 g/mL, about 0.3 g/mL to about 0.8 g/mL, or about 0.5 g/mL to about 0.7 g/mL). Bulk density of the granules can be determined using methods known in the art, for example, by pouring the granules into a graduated cylinder of a suitable size.

The granules prepared by the present methods can have a tapped density of about 0.5 g/mL to about 1.2 g/mL, or about 0.7 g/mL to about 0.9 g/mL. Tapped density of the granules can be determined using methods known in the art, for example, using a tapped volumeter to compact the granules using 100-tap increments until volume change was less than 5%.

The granules prepared by the methods described herein can have an improved flowability (e.g., as reflected by Carr's index, Hausner ratio, angle of repose, or bulk and/or tapped density) compared to the pre-blend composition of step (i). The granules can also have an improved flowability compared to the first composition comprising sodium phenylbutyrate and/or the second composition comprising TURSO. In some embodiments, the granules prepared by the present methods have a Carr's index of about 12 or less (e.g., a Carr's index of about 1 to 12, e.g., about 11, 10, 9, 8, 7, 6, or about 5). The processing methods described herein can result in a decrease of at least about 3 (e.g., at least about 4, 5, 6, 7, 8, or 10) in the Carr's index of the granules formed in step (ii) as compared to the Carr's index of the pre-blend composition from step (i).

In some embodiments of any of the methods of processing a composition provided herein, the dissolution time for releasing about 75% of the TURSO in the granules formed in step (iii) is between about 0.5 to about 15 minutes (e.g., between about 0.5 to about 10 minutes, between about 0.5 to about 8 minutes, or between about 0.5 to about 5 minutes). In some embodiments, the dissolution time for releasing about 75% of the sodium phenylbutyrate in the granules formed in step (iii) is between about 0.5 to about 15 minutes (e.g., between about 0.5 to about 10 minutes, between about 0.5 to about 8 minutes, or between about 0.5 to about 5 minutes). Methods of determining dissolution time of a compound can be determined using methods known in the art.

In some embodiments of any of the methods of processing a composition provided herein, the composition further includes about 8% to about 24% w/w (e.g., any of the subranges of this range described herein) of dextrates; about 1% to about 6% w/w (e.g., any of the subranges of this range described herein) of sugar alcohol (e.g., any of the sugar alcohols described herein or known in the art, e.g. sorbitol); and about 22% to about 35% w/w (e.g., any of the subranges of this range described herein) of maltodextrin. The composition can further include about 0.5% to about 5% w/w (e.g., any of the subranges of this range described herein) of sucralose, about 2% to about 15% w/w (e.g., any of the subranges of this range described herein) of one or more flavorants, about 0.05% to about 2% w/w (e.g., any of the subranges of this range described herein) of porous silica, about 0.5% to about 5% w/w (e.g., any of the subranges of this range described herein) of a buffering agent (e.g., any of the buffering agents described herein or known in the art, e.g. sodium phosphate), and/or about 0.05% to about 1% w/w (e.g., any of the subranges of this range described herein) of one or more lubricants (e.g., any of the lubricants described herein or known in the art, e.g. sodium stearyl fumarate).

EXAMPLES

Additional embodiments are disclosed in further detail in the following examples, which are provided by way of illustration and are not in any way intended to limit the scope of this disclosure or the claims.

Example 1: Flow Optimization by Alteration of Sorbitol, Dextrates and Sodium Phosphate Type The following experiments were conducted to develop and optimize the formulation and related processes to produce a final dosage form containing dual active pharmaceutical ingredients (APIs, TURSO and NaPB) and taste-blinded placebos. Formulation development involved optimization of blend flow properties using various excipients, taste-masking of active and placebo blends, and moisture control using excipients and processing techniques. A placebo formulation mimicking the active formulation in both appearance and taste was developed using a similar process.

As both APIs were determined to be poorly flowing which would increase the difficulty of automated processing during scale up and production, flow optimization was conducted by blending the APIs with better flowing excipients with the dual purpose of both improving blend flow for processing and taste-masking the APIs.

Materials and Equipment

TABLE 1

Materials used for characterization of flow properties

| Material | Brand | Grade | Manufacturer | Manufacturer Lot # |
|---|---|---|---|---|
| TURSO | — | — | Prodotti Chimici E Alimentari S.p.A. | 2015010026 |
| NaPB | — | — | Sri Krishna Pharmaceuticals limited | SPB013/14-15 |
| Sodium Phosphate Monobasic Monohydrate | — | ACS | Fisher Chemical | 116745 |
| Sodium Phosphate Dibasic Anhydrous | — | ACS | Amresco | 2934C448 |
| Dextrates | Emdex | NF | JRS Pharma | EX13K42DX |
| Sorbitol | Neosorb P110 | USP/NF/EP/JP | Roquette | US061 |
| Sucralose | — | HPLC | Sigma Life Science | BCBH2029V |
| Colloidal Silica | Aerosil 200 | USP/NF/EP/JP | Spectrum | RM-08L13 |
| Magnesium Stearate | Ligamed MF-2-K | USP/NF/EP/JP | Peter Greven | C401433 |

TABLE 2

Equipment

| Equipment | Manufacturer | Model |
|---|---|---|
| Sieve Shaker | W.S. Tyler | RX86 |
| Sieves | Fischer Scientific | E-11 spec |
| Tapped Volumeter | Erweka | SVM22 |
| LOD | Denver Instruments | IR-30 |

TABLE 3

Blends with varying sorbitol and dextrate amounts
Target Weights (x2 sachets)

| | | Formulation # | | | Formulation % | | |
|---|---|---|---|---|---|---|---|
| Material | Lot # | A | B | C | A | B | C |
| TURSO | 2015010026 | 2 | 2 | 2 | 14.7 | 12.8 | 11.3 |
| NaPB (Sri Krishna Pharmaceuticals limited) | SPB013/ 14-15 | 6 | 6 | 6 | 44 | 38.4 | 34 |
| Monosodium phosphate monohydrate (Fisher Chemical) | 116745 | 0.56 | 0.56 | 0.56 | 4.1 | 3.58 | 3.17 |
| Disodium phosphate, anhydrous (Amresco) | 2934C448 | 0.784 | 0.784 | 0.784 | 5.75 | 5.01 | 4.44 |
| Dextrates, hydrated (Emdex NF) | EX13K42DX | 3.2 | 4.8 | 6.4 | 23.5 | 30.7 | 36.3 |
| Sorbitol (Neosorb p110) | US061 | 0.8 | 1.2 | 1.6 | 5.86 | 7.67 | 9.07 |
| Sucralose (Sigma Life Science, 69293-100g) | BCBH2029V | 0.02 | 0.02 | 0.02 | 0.15 | 0.13 | 0.11 |
| Aerosil 200 (Evonik) | RM-08L13 | 0.16 | 0.16 | 0.16 | 1.17 | 1.02 | 0.91 |
| Magnesium Stearate (Peter Greven, Ligamed MF-2-k) | C401433 | 0.12 | 0.12 | 0.12 | 0.88 | 0.77 | 0.68 |
| Total: | | 13.64 | 15.64 | 17.644 | 100 | 100 | 100 |

Results

Formulations A, B, and C were prepared which contain varying sorbitol and dextrate amounts. The formulations were then subjected to the following analyses.

Particle Size Distribution

Sample blends were analyzed using a W.S. Tyler RX86 sieve shaker fitted with #60, 80, 100, 140, 200, 325, or 400 mesh screens. 10 g of each API was placed into the topmost sieve and was agitated for 5 minutes, after which the amount of API collected in each sieve was measured and recorded. The particle size distribution of NaPB and TURSO are shown in FIG. 1.

Hausner Ratio and Carr's Index

Bulk density was calculated for each API and blend by gently pouring powder into a 25 mL graduated cylinder. Tapped density was calculated using a tapped volumeter to compact each powder using 100-tap increments until volume change was <5%. Hausner ratio and Carr's index were then calculated using bulk density and tapped density. The Carr's index of the APIs and formulations A-C are shown in Table 4 below. Formulation C was selected based on flow characteristics. Carr's index, in addition to being a measure of compressibility, may also be used to determine the flow properties of a material. A high Carr's index (large difference in bulk versus tapped densities) indicates that the material has stronger intermolecular forces which reduces flowability. Acceptable flow property (as determined by the packaging equipment used) was a minimum of a Carr's index of under 25, with a Carr's index of below 20 being preferable.

TABLE 4

Carr's index of APIs and blends

| Flow characteristic | Carr's index | NaPB | TURSO | Formulation A | Formulation B | Formulation C |
|---|---|---|---|---|---|---|
| Excellent | <10 | — | — | — | — | — |
| Good | 11-15 | — | — | — | — | — |
| Fair | 16-20 | — | — | — | — | 19.2 |

TABLE 4-continued

Carr's index of APIs and blends

| Flow characteristic | Carr's index | NaPB | TURSO | Formulation A | Formulation B | Formulation C |
|---|---|---|---|---|---|---|
| Passable | 21-25 | — | 24.2 | 21.5 | 23.1 | — |
| Poor | 26-31 | — | — | — | — | — |
| Very poor | 32-37 | — | — | — | — | — |
| very very poor | >38 | 39.2 | — | — | — | — |

Angle of Repose

Next, flowability of formulation C was measured using angle of repose, determined by allowing powder to fall from a fixed-height funnel onto a flat surface. Angle of repose was calculated using the radius of the base of the pile and the height. The angle of repose for formulation C was determined to be 31.1. For reference, the flow characteristics that correspond with a certain range of angle of repose are shown in Table 5 below.

TABLE 5

Angle of Repose and flow characteristics

| Angle of Repose | Flow characteristic |
|---|---|
| 25-30 | Excellent |
| 31-35 | Good |
| 36-40 | Fair |
| 41-45 | Passable |

TABLE 5-continued

Angle of Repose and flow characteristics

| Angle of Repose | Flow characteristic |
| --- | --- |
| 46-55 | Poor - must vibrate |
| 56-65 | Very poor |
| >66 | very very poor |

Blend Agglomeration

After storage in sealed bottles for about one week, slight agglomeration of blends was observed. Results from loss-on-drying (LOD) testing of sorbitol and dextrates showed that neither exhibited massive water uptake, and they were unlikely to be the cause for agglomeration.

Prior to finalizing the formulation, dibasic sodium phosphate in the formulation was changed from anhydrous to heptahydrate, due to concerns that the anhydrous form was more hygroscopic than the heptahydrate form.

Formulation Selection

Sorbitol and dextrate levels from formulation C were selected due to significant improvements in flow properties as measured by angle of repose and Carr's index.

Example 2: Taste Masking Optimization

To produce a palatable dosage form that could be consumed by patients with possible motor impairment, a powder for reconstitution dosage form was selected and various sweeteners and flavors were investigated for taste masking.

Materials

TABLE 6

Materials for taste masking optimization

| Material | Lot # | Manufacturer |
| --- | --- | --- |
| TURSO | 2015010026 | Prodotti Chimici E Alimentari S.p.A. |
| NaPB | SPB013/14-15 | Sri Krishna Pharmaceuticals |
| Sodium phosphate monobasic, monohydrate | 116745 | Fisher Chemical |
| Sodium phosphate dibasic, anhydrous | 2934C448 | Amresco |
| Dextrates, hydrated (Emdex NF) | EX13K42DX | JRS Pharma |
| Sorbitol (Neosorb p110) | US061 | Roquette |
| Sucralose (69293-100 g) | BCBP3048V | Sigma Life Science |
| Aerosil 200 | RM-08L13 | Evonik |
| 26-04-0026SD1 Peach Flavor Powder (Nat & Art) | 021716 | Edgar A. Weber & Co. |
| 28-05-0050SD1 Peach Flavor Powder (MWNI) | 010616 | Edgar A. Weber & Co. |
| 28-98-0014SD1 Strawberry Flavor Powder (MWNI) | 012516 | Edgar A. Weber & Co. |
| 30-86-0184SD1 Strawberry Flavor Powder (Art) | 072815 | Edgar A. Weber & Co. |
| 20-85-4724SD1 Orange Flavor Powder (Nat) | 021716 | Edgar A. Weber & Co. |
| 26-01-0120SD2 Orange Flavor Powder (Nat & Art) | 080715 | Edgar A. Weber & Co. |
| 26-03-0039SD1 Mango Flavor Powder (Nat & Art) | 021716 | Edgar A. Weber & Co. |
| 28-11-0058SD1 Mango Flavor Powder (MWNI) | 011916 | Edgar A. Weber & Co. |
| 30-98-0057SD1 Apple Flavor Powder (Art) | 072915 | Edgar A. Weber & Co. |
| 22-97-0119SD2 Apple Flavor Powder (WONF) | 030216 | Edgar A. Weber & Co. |
| F4538 Grape Flavor Powder (Art) | 45383316 | Foote & Jenks |
| Hawaiian Punch Flavor Powder (Nat) | 158D12 | Prinova |
| S Blue Raspberry Flavor ) Powder (Nat & Art | 113D01 | Prinova |
| Mixed Berry Flavor Powder (Nat) | 118D01 | Prinova |
| Cherry Flavor Powder (Nat & Art) | 186D01 | Prinova |
| 28-03-0212SD1 Mixed Berry Flavor Powder (MWNI) | 031516 | Edgar A. Weber & Co. |
| Kleptose Linecaps Maltodextrin | E436F | Roquette |

Results

Sucralose Level Optimization

Formulation C was produced with varying levels of sucralose (formulations C1-C3) for taste masking. The compositions of formulations C1-C3 are shown in Table 7. Formulation C1 was selected based on best taste-masking performance.

TABLE 7

Sucralose formulation compositions

| Material (Formulation C) | Form C1 (0.5% sucralose) | C1 by % | Form C2 (0.3% sucralose) | C2 by % | Form C3 (0.1% sucralose) | C3 by % |
| --- | --- | --- | --- | --- | --- | --- |
| TURSO | 1.0000 | 14.74% | 1.0000 | 14.77% | 1.0000 | 14.80% |
| NaPB | 3.0000 | 44.21% | 3.0000 | 44.30% | 3.0000 | 44.39% |
| Sodium phosphate monobasic, monohydrate | 0.2800 | 4.13% | 0.2800 | 4.13% | 0.2800 | 4.14% |
| Sodium phosphate dibasic, anhydrous | 0.3920 | 5.78% | 0.3920 | 5.79% | 0.3920 | 5.80% |
| Dextrates, hydrated | 1.6000 | 23.58% | 1.6000 | 23.63% | 1.6000 | 23.67% |
| Sorbitol | 0.4000 | 5.89% | 0.4000 | 5.91% | 0.4000 | 5.92% |
| Aerosil 200 | 0.0800 | 1.18% | 0.0800 | 1.18% | 0.0800 | 1.18% |
| Subtotal: | 6.7520 | 99.50% | 6.7520 | 99.70% | 6.7520 | 99.90% |
| Sucralose | 0.0339 | 0.50% | 0.0203 | 0.30% | 0.0068 | 0.10% |
| Total: | 6.7859 | 100.00% | 6.7723 | 100.00% | 6.7588 | 100.00% |

Flavoring Selection

Bulk active blend was prepared and dissolved in about 250 mL water per dosage unit. Several flavoring agents were added in varying concentrations in addition to Kleptose Linecaps Maltodextrin until the desired level of taste-masking was reached. The final flavors and sweetener concentrations were selected based on taste optimization.

Maltodextrin Use and Updated Formulation

To maintain the formulation as having around 10 g of total material with the addition of flavorants and maltodextrin, all other materials (except API) were adjusted and formulation C1 was further modified. Further, dibasic sodium phosphate in the formulation was changed from anhydrous to heptahydrate, due to concerns that the anhydrous form was more hygroscopic than the heptahydrate form. The modified formulation C1 is shown in Table 8 below.

TABLE 8

Modified formulation C1

| Material (Modified formulation C1) | % Composition (W/W) | Modified formulation C1- 1 sachet (0.5% sucralose) |
|---|---|---|
| TURSO | 9.35% | 1 |
| NaPB | 28.06% | 3 |
| Sodium phosphate monobasic, monohydrate | 2.62% | 0.28 |
| Sodium phosphate dibasic, Heptahydrate | 6.92% | 0.74 |
| Dextrates, hydrated | 14.96% | 1.6 |
| Sorbitol | 3.74% | 0.4 |
| Aerosil 200 | 0.75% | 0.08 |
| Sucralose | 0.50% | 0.0535 |
| Mixed Berry Flavoring (0.14% W/V) | 3.10% | 0.331223 |
| Subtotal: | 70.00% | 7.484723 |
| Kleptose Linecaps (Maltodextrin) | 30.00% | 3.207738429 |
| Total: | 100.00% | 10.69246143 |

Of note, flow characteristics remained substantially stronger than the flow of the APIs suggesting that this altered formulation was still successful at improving flow. The Carr's index for the modified formulation C1 was 22.3, with the angle of repose being 34.4. For reference, the flow characteristics that correspond with a certain range of angle of repose are shown in Table 5 above; the flow characteristics that correspond with a certain range of Carr's index are shown in Table 9.

TABLE 9

Carr's index and Flow Characteristics

| Carr's index | Flow characteristic |
|---|---|
| <10 | Excellent |
| 11-15 | Good |
| 16-20 | Fair |
| 21-25 | Passable |
| 26-31 | Poor |
| 32-37 | Very poor |
| >38 | very very poor |

Results

Addition of specific flavorants and maltodextrin as well as levels of sucralose were tested to ensure optimal taste masking. Further, addition of these agents did not impact the improved flowability achieved in Example 1.

Example 3: Agglomeration Discovery and Prevention

Materials and Equipment

TABLE 10

Active Stability Materials

| Material | Brand | Grade | Manufacturer | Manufacturer Lot # |
|---|---|---|---|---|
| TURSO | — | — | Prodotti Chimici E Alimentari S.p.A. | 2015010026 |
| NaPB | — | — | Sri Krishna Pharmaceuticals | SPB026/ 14-15 |
| Sodium Phosphate Monobasic Monohydrate | — | ACS | Amresco | 1575C229 |
| Sodium Phosphate Dibasic Heptahydrate | — | ACS | Amresco | 3606C403 |
| Dextrates, hydrated | Emdex | NF | JRS Pharma | EX13K42DX |
| Sorbitol | Neosorb P110 | USP/NF/ EP/JP | Roquette | US061 |
| Sucralose | — | HPLC | Sigma Life Science | BCBP3048V |
| Colloidal Silica | Aerosil 200 | USP/NF/ EP/JP | Spectrum | 1DK0436 |
| Maltodextrin, Lab4118 | Kleptose Linecaps | EP | Roquette | E436F |
| Mixed Berry Flavor Powder (MWNI) | 28-03- 0212SD1 | — | Edgar A. Weber & Co. | 031516 |

TABLE 11

Equipment used for active stability lot production

| Equipment | Manufacturer | Model |
|---|---|---|
| Blender | Bohle | LM40 w/5 L bin |

TABLE 12

Equipment used for analysis of batch failure

| Equipment | Manufacturer | Model |
|---|---|---|
| LOD | Denver Instruments | IR-30 |
| Stability Chamber | Environmental Specialties | ES2000/ES2000 Reach-in |

Results

Storing the blend for ~36 hours inside a sealed Bohle Blender 5 L Bin resulted in agglomeration and difficulties in dispensing the blend. To prevent agglomeration and further improve blend stability, the agglomerated blend was manually removed and placed in a 50° C. drying oven and subjected to Loss on Drying (LOD) testing.

Loss on Drying (LOD) Testing

LOD testing was performed on recovered agglomerated blend (PD2016-015-33B) after ~2 hours of drying at 50° C. to determine the degree of moisture uptake. Results were compared against a non-agglomerated blend that had been stored in a sealed bottle (PD2016-015-29A). The results of the LOD testing are shown in Table 13.

TABLE 13

| Blend Batch | Sample Weight(g) | % Loss on Drying | Time (min) |
|---|---|---|---|
| PD2016-015-33B (agglomerated) | 2.044 | 5.72 | 7.7 |
|  | 2.215 | 5.6 | 4.7 |
|  | 2.121 | 6.22 | 7.1 |
|  | 2.09 | 6.22 | 10 |
| PD2016-015-29A | 2.234 | 4.59 | 6.9 |
|  | 2.205 | 4.63 | 7.4 |

Dynamic Vapor Sorption (DVS) Testing

Figure 2:
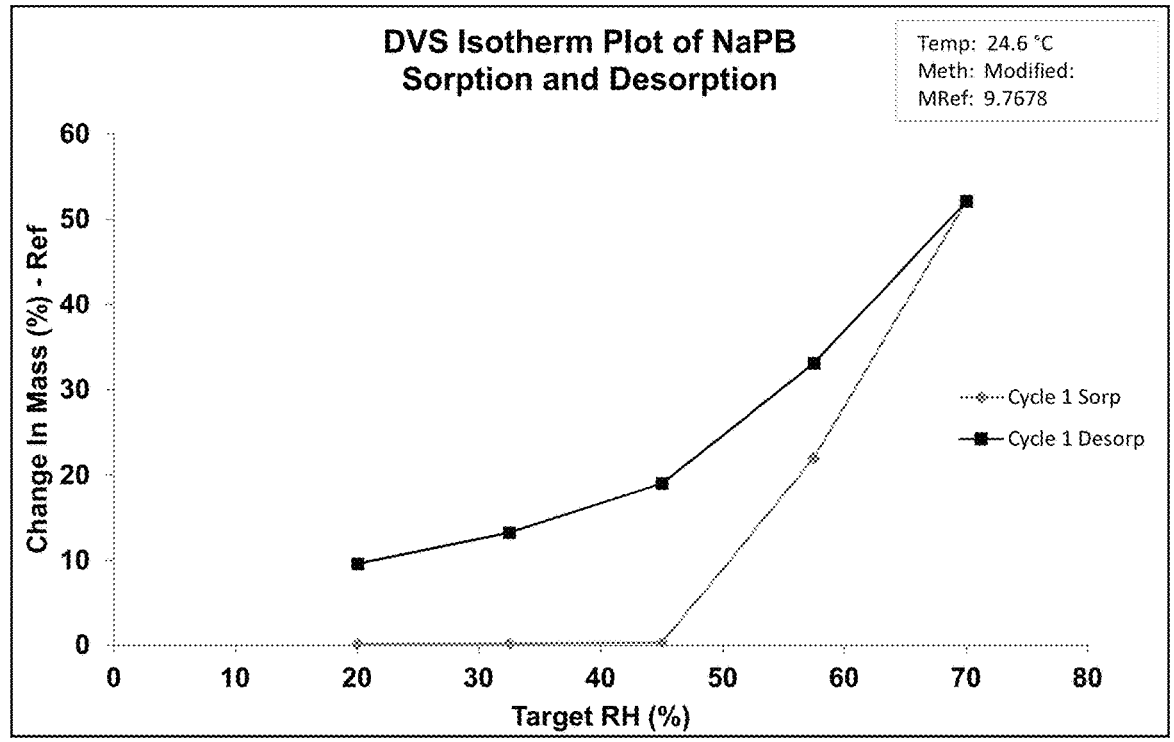
FIG. 2 is a DVS isotherm plot of sodium phenylbutyrate sorption and desorption.
Figure 3:
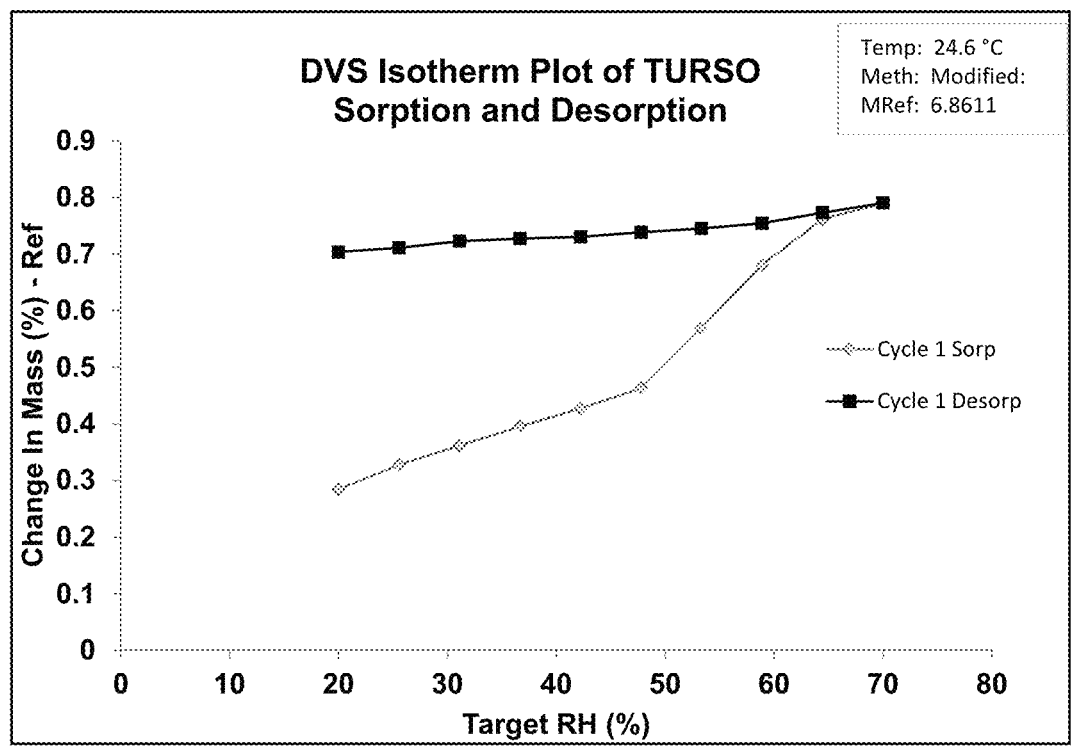
FIG. 3 is a DVS isotherm plot of TURSO sorption and desorption.
Figure 4:
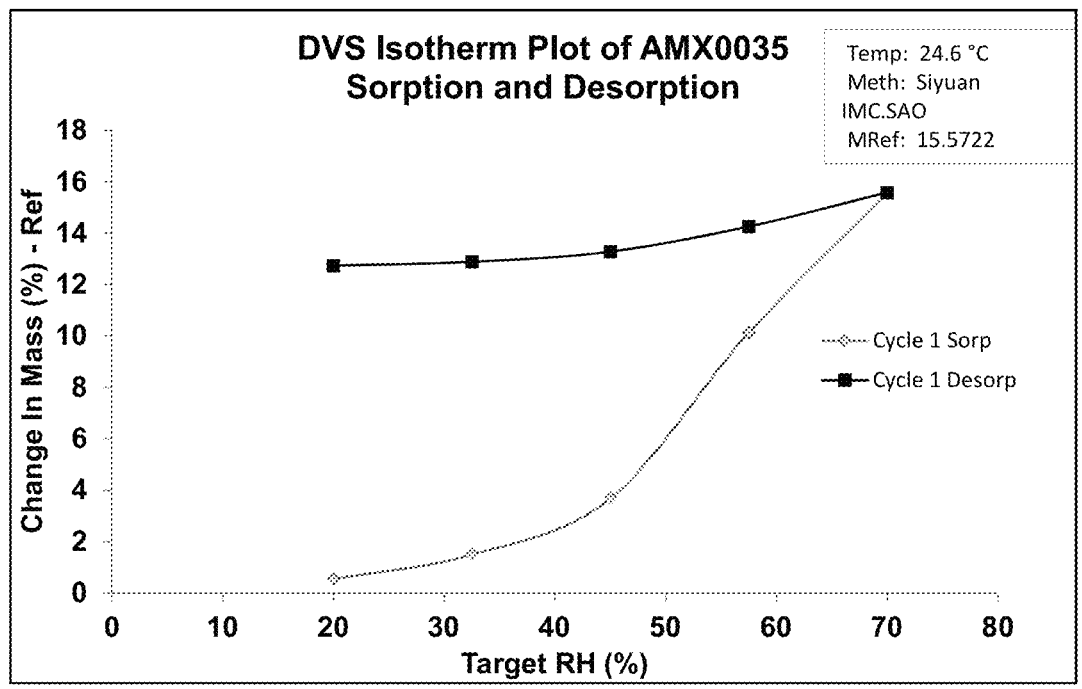
FIG. 4 is a DVS isotherm plot showing sorption and desorption of the active blend.

Samples of NaPB, TURSO, and modified formulation C1 blend were subjected to DVS testing to determine the magnitude of weight gain due to humidity. The DVS isotherm plots for NaPB and TURSO are shown in FIGS. 2 and 3, respectively. The results showed that above 45% RH, NaPB exhibited massive fluctuations in mass. These changes in mass were also reflected in the active blend (as shown in FIG. 4), and were believed to contribute to the observed agglomeration.

Effect of Humidity on APIs Separately and Combined

Samples of NaPB, TURSO, and a blend of both were stored in open top vials at 25° C./60% RH for ~60 hours, after which the vials were removed and observations recorded.

Agglomeration occurred in blends containing both APIs upon moisture uptake. Fluctuations in the mass of NaPB up to 50% and agglomeration presents processing and dosing difficulties as moisture uptake would result in changes in potency, and agglomerated material would be limited in its ability to blend and flow during processing. Since agglomeration was only observed when the two APIs were exposed to each other in the presence of moisture, prevention of moisture uptake or separation of APIs were needed to reduce agglomeration. The following experiments were performed with the aim of reducing agglomeration.

Equilibration and Roller Compaction

Materials and Equipment

TABLE 14

Materials for equilibration Study

| Material | Brand | Grade | Manufacturer | Manufacturer Lot # |
|---|---|---|---|---|
| TURSO | — | — | Prodotti Chimici E Alimentari S.p.A. | 2015010026 |
| NaPB | — | — | Sri Krishna Pharmaceuticals | SPB026/14-15 |
| Sodium Phosphate Monobasic Monohydrate | — | ACS | Amresco | 1575C229 |
| Sodium Phosphate Dibasic Heptahydrate | — | ACS | Amresco | 3606C403 |
| Dextrates, hydrated | Emdex | NF | JRS Pharma | EX13K42DX |
| Sorbitol | Neosorb P110 | USP/NF/EP/JP | Roquette | US782 |
| Colloidal Silica | Aerosil 200 | USP/NF/EP/JP | Spectrum | 1DK0436 |
| Maltodextrin, Lab4118 | Kleptose Linecaps | EP | Roquette | E436F |
| Mixed Berry | 28-03- | — | Edgar A. | 031516 |
| Flavor Powder (MWNI) | 0212SD1 | | Weber & Co. | |

TABLE 15

Equipment for equilibration Study

| Equipment | Manufacturer | Model |
|---|---|---|
| Blender | Bohle | LM40 w/5 L bin |
| Comil Conical Mill | Quadro | 197 |
| Sieve (#30 mesh) | Fischer Scientific | E-11 spec |
| Roller Compactor | Gerteis | Mini-Pactor |
| Heat Sealer | Midwest Pacific | MP-12 |
| Karl Fischer Coulometer | Mettler Toledo | DL32 Coulometer |

Equilibration

API equilibration: To test whether equilibration could prevent later agglomeration, the APIs were allowed to equilibrate to ambient conditions. Briefly, the APIs were laid out in 2 separate trays to equilibrate. Samples were taken at T=0, 1, 2, 3, 4, and 24 hours and sealed into headspace vials for analysis by Karl Fischer Titration. This study was performed to determine the rate of moisture absorption for each API and to determine if pre-equilibrated APIs would result in less agglomeration due to reduced moisture uptake after blending.

Water content analysis by Karl Fischer Titration: Each sample was analyzed for water content using Karl Fischer Titration. Equilibration was determined when RSD was found to be <10% between two consecutive time points.

Blending Parameters: Each batch was blended for 20 minutes, milled, and then blended an additional 20 minutes at 25 RPM. For milling, a Quadro Comil fitted with a scalloped 1016 conical mesh screen was operated at 30% power. Non-granulated test sachets were filled.

Roller Compaction

Dry granulation by roller compaction of the active blend was performed. The remaining blend was roller compacted at 7.5 and 10 kN. Test sachets of each granulation condition were filled to observe the behavior of granulated and non-granulated samples in packaging over time. Table 16 below shows the roller compaction parameters used.

TABLE 16

Roller compaction parameters

| Parameter | Setting |
|---|---|
| Press Force | 7.5/10 kN |
| Roll Speed | 3 RPM |
| Gap Size | 2.5 mm |
| Granulation Screen | 2.0 mm |
| Granulation Speed | 10/20 RPM |

Results from the equilibration study demonstrated that equilibration surprisingly had no significant effect on API moisture content. All blends and granules agglomerated over time; however, 10 kN granules showed the least agglomeration and best recovery from sachets, suggesting that roller compaction surprisingly resulted in large improvements in agglomeration prevention.

Example 4: Silica Processing Study for Agglomeration Prevention

A study was also performed to determine if agglomeration was due to interactions between the two APIs and if porous silica could be used to reduce agglomeration by controlling local moisture. Tables 17 and 18 below show the materials used for the separate API processing and silica study.

TABLE 17

Materials for Separate API Processing/Silica Study

| Material | Brand | Grade | Manufacturer Lot # | Manufacturer |
|---|---|---|---|---|
| TURSO | — | — | 2016020063 | Prodotti Chimici E Alimentari S.p.A. |
| NaPB | — | — | SPB013/ 14-15 | Sri Krishna Pharmaceuticals |
| Sodium phosphate dibasic, Anhydrous | — | ACS | 2934C448 | Amresco |
| Dextrates, hydrated | Emdex | NF | EX13K42DX | JRS Pharma |
| Sorbitol | Neosorb P110 | USP/NF/ EP/JP | US782 | Roquette |
| Sucralose (69293-100 g) | — | HPLC | BCBP3048V | Sigma Life Science |
| Colloidal Silica | Aerosil 200 | USP/NF/ EP/JP | 1DK0436 | Spectrum |
| Silica | Syloid 244FP | USP/NF | 5210156995 | Grace |
| Maltodextrin, Lab4118 | Kleptose Linecaps | EP | E436F | Roquette |
| Mixed Berry Flavor Powder (MWNI) | 28-03-0212SD1 | — | 031516 | Edgar A. Weber & Co. |
| Sodium Stearyl Fumarate | Pruv | NF | 1298X | JRS Pharma |
| Silica | Syloid 63FP | USP/NF | 5210151493 | Grace |

TABLE 18

Equipment for Separate API Processing/Silica Study

| Equipment | Manufacturer | Model |
|---|---|---|
| Roller Compactor | Gerteis | Mini-Pactor |
| Tapped Volumeter | Erweka | SVM22 |
| Heat Sealer | Midwest Pacific | MP-12 |
| Sieve Shaker | W.S. Tyler | RX86 |
| Sieves | Fischer Scientific | E-11 spec |

Each API was blended and roller compacted with excipients separately to determine if the proximity of the dual APIs in the blend or granules was responsible for agglomeration. The resulting granules were then recombined and blended before filling test sachets. Bulk and tapped densities of each blend were measured prior to roller compaction. For this experiment, all silica were used at 1% W/W. Aerosil 200 was used as a negative control while Syloid 244FP and Syloid 63FP were used to remove moisture from the APIs to determine if APIs would agglomerate with reduced local levels of water. The flow characterization of the blends are shown in Table 19 below.

TABLE 19

Flow Characterization of Silica Study Blends

| | 1% Aerosil 200 | 1% Syloid 244FP | 1% Syloid 244FP (TURSO) |
|---|---|---|---|
| Bulk Density (g/mL) | 0.4906 | 0.5313 | 0.6429 |
| Tapped Density (g/mL) | 0.6500 | 0.6846 | 0.8372 |
| Hausner Ratio | 1.3250 | 1.2885 | 1.3023 |
| Carr Index | 24.5283 | 22.3881 | 23.2143 |

| | 1% Syloid 244FP (NaPB) | 1% Syloid 63FP (TURSO) | 1% Syloid 63 FP (NaPB) |
|---|---|---|---|
| Bulk Density (g/mL) | 0.5517 | 0.6032 | 0.5079 |
| Tapped Density (g/mL) | 0.6809 | 0.8130 | 0.6400 |
| Hausner Ratio | 1.2340 | 1.3478 | 1.2600 |
| Carr Index | 18.9655 | 25.8065 | 20.6349 |

Particle Size Distribution

Figure 5:
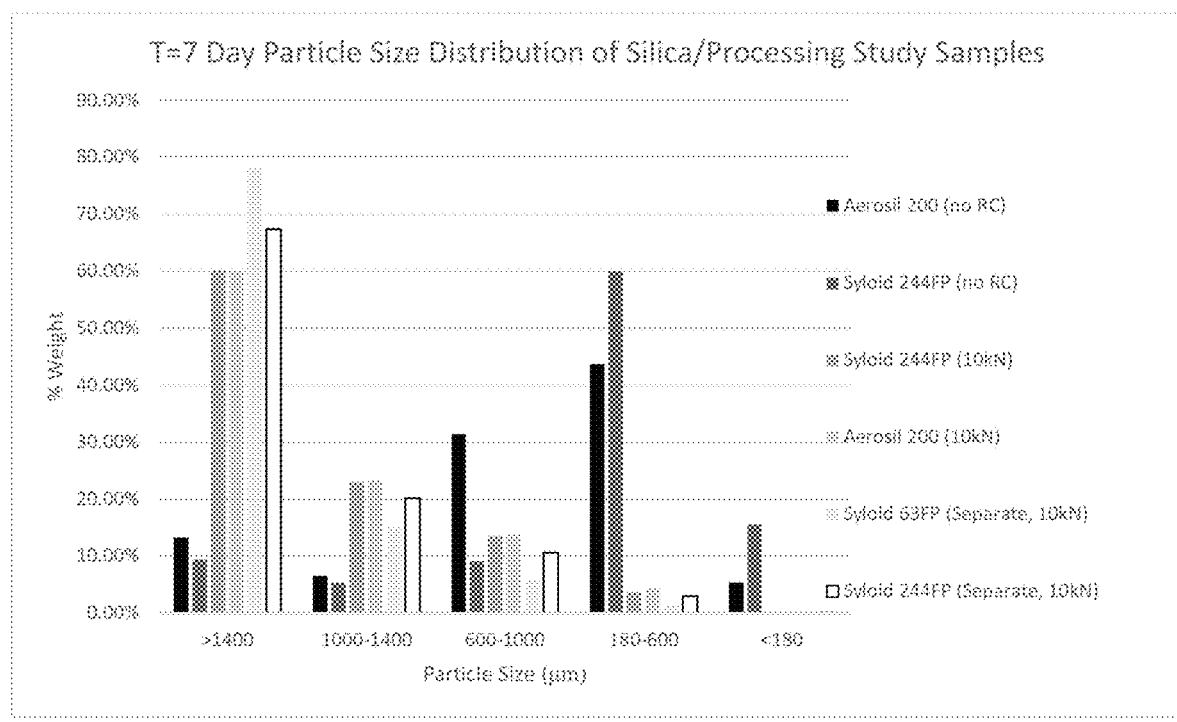
FIG. 5 shows particle size distribution of blends that contain different silica types.

Particle size distribution was used as a measure of agglomeration as agglomerated particles would be unable to pass through smaller sieve sizes, resulting in a distribution skewed towards larger particles. Sieve shaker analysis was performed at T=7 days for each test condition. The results are shown in FIG. 5.

Angle of Repose

Flowability as measured by angle of repose was used to determine relative degree of agglomeration for each condition. As flowability was seen to decrease in agglomerated samples, a low angle of repose could signify low levels of agglomeration and better recovery from packaging of the final product. Angle of repose measurements were taken for each test condition at T=4 (Table 20).

TABLE 20

Angle of Repose at T = 4

| Flow Characteristic | Angle of Repose | Aerosil 200 (no RC) | Syloid 244FP (no RC) | Syloid 244FP (10 kN) | Aerosil 200 (10 kN) | Syloid 63FP (Separate, 10 kN) | Syloid 244FP (Separate, 10 kN) |
|---|---|---|---|---|---|---|---|
| Excellent | 25-30 | — | — | — | — | — | — |
| Good | 31-35 | 35.69 | 35.71 | 34.38 | 33.05 | 31.83 | 34.05 |
| Fair | 36-40 | — | — | — | — | — | — |
| Passable | 41-45 | — | — | — | — | — | — |
| Poor-Must Vibrate | 46-55 | — | — | — | — | — | — |
| Very Poor | 56-65 | — | — | — | — | — | — |
| Very, Very Poor | >66 | — | — | — | — | — | — |

Results

Originally, Aerosil 200, a form of silica was used in the formulation resulting in angle of repose of 35.69. Switching this material to syloid 63FP and roller compacting at 10 kN press force resulted in an 11% improvement in flow. Surprisingly, a different syloid product, syloid 244FP did not produce the same improvement. As a result of these experiments, aerosol 200 was switched out of the formulation in exchange for syloid 63FP and roller compaction was added to the process. Given the detrimental effects of agglomeration for processing, the 11% improvement represented a significant and surprising advance.

Example 5: Production of Stability/Tooling Batches for Active Formulation

Active Formulation Blending and Roller Compaction: Tables 21 and 22 show the materials and equipment used for active formulation blending and roller compaction. Table 23 shows the active formulation.

TABLE 21

| Material | Brand | Grade | Manufacturer | Manufacturer Lot # |
|---|---|---|---|---|
| TURSO | — | — | Prodotti Chimici E Alimentari S.p.A. | 2016020063 |
| NaPB | — | — | Sri Krishna Pharmaceuticals limited | SPB011/15-16 |
| Sodium Phosphate Dibasic Anhydrous | — | ACS | Amresco | 3536C204 |
| Dextrates | Emdex | NF | JRS Pharma | EX15J37D |
| Sorbitol | Neosorb P110 | USP/NF/EP/JP | Roquette | US453 |
| Sucralose | — | HPLC | Sigma Life Science | BCBP3048V |
| Silica | Syloid 63FP | USP/NF | Grace | 5210151493 |
| Maltodextrin | Kleptose Linecaps | EP | Roquette | E436F |
| Mixed Berry Flavor Powder (MWNI) | 28-03-0212SD1 | — | Edgar A. Weber & Co. | 1609834 |
| Sodium Stearyl Fumarate | Pruv | NF | JRS Pharma | 1298X |

TABLE 22

| Equipment | Manufacturer | Model |
|---|---|---|
| Sieve (#30 mesh) | Fischer Scientific | E-11 spec |
| Blender (w/20 L bin) | Bohle | LM40 |
| Comil Conical Mill | Quadro | 197 |
| Roller Compactor | Gerteis | Mini-Pactor |
| Heat Sealer | Midwest Pacific | MP-12 |

TABLE 23

| Material (Active Blend- 1salt) | % Composition (W/W) | Active Blend-x1 (unit:gram) |
|---|---|---|
| TURSO | 10.29% | 1.0000 |
| NaPB | 30.86% | 3.0000 |
| Sodium phosphate dibasic, Anhydrous | 2.88% | 0.2800 |
| Dextrates, hydrated | 16.46% | 1.6000 |
| Sorbitol | 4.11% | 0.4000 |
| Syloid 63FP (1%) | 1.00% | 0.0971 |
| Sucralose (0.5%) | 0.50% | 0.0485 |
| Sodium Stearyl Fumarate (0.5%) | 0.50% | 0.0485 |
| Mixed Berry Flavoring (0.14% W/V) | 3.41% | 0.3312 |
| Subtotal: | 70.00% | 6.8053 |
| Kleptose Linecaps (30%) | 30.00% | 2.9166 |
| Total: | 100.00% | 9.7219 |

All materials were weighed, sieved (#30 mesh) and layered into a 20 L blender bin before blending for 30 minutes at 25 RPM. Blender contents were discharged and milled using a Quadro Comil operating at 30% speed and fitted with a 1016 scalloped mesh conical screen. Following milling, the blend was placed back into the blender bin to blend for an additional 30 minutes at 25 RPM. During the final 30 minutes of blending, blend uniformity samples were taken at 10 minute intervals and analyzed by HPLC for API content. Once RSD was shown to be >5% and drug load values were within 90-110%, the blend was roller compacted using the parameters shown in Table 24 below. Under these parameters, a batch was successfully produced.

TABLE 24

Roller Compaction Parameters

| Parameter | Setting |
|---|---|
| Press Force | 7.5/10 kN |
| Roll Speed | 3 RPM |
| Gap Size | 2.5 mm |
| Granulation Screen | 2.0 mm |
| Granulation Speed | 10/20 RPM |

Example 6: Further Flavor Optimization

While the flavor optimization in Example 2 substantially improved taste, a follow-up set of experiments were conducted to determine if taste could be even further improved.

Additional Flavorants

A series of new flavorants were tested, including mango, strawberry, masking flavor and mixed berry flavor. After additional taste testing, a combination of the masking flavor and mixed berry flavors was determined to be optimal for masking the taste of the APIs. The result was a substantial improvement over formulation C1, which was developed during the initial round of formulation development.

Additional Sucralose

Following the change in flavorants, the level of sucralose was further adjusted and subjected to taste testing. It was determined that additional sucralose further improved/masked the taste of the APIs, and the sucralose level was revised to 200 mg per unit dose.

Formulation D

With the above changes, the formulation was revised to formulation D (Table 25) which had improved taste characteristics.

TABLE 25

| Formulation D | | |
|---|---|---|
| Material | Milligram per unit dose | wt % |
| NaPB | 3000.000 | 29.2% |
| TURSO | 1000.000 | 9.7% |
| Dextrates Hydrated NF (EMDEX NON GMO) | 1600.000 | 15.6% |
| Sorbitol NF (NEOSORB P110) | 400.000 | 3.9% |
| Sucralose NF/PH.EUR | 200.000 | 1.9% |
| Silicon Dioxide NF (Syloid 63FP)-CTM | 97.200 | 0.09% |
| Maltodextrin NF/PH.EUR. (Kleptose) | 2916.000 | 28.3% |
| Mixed Berry Flavor Powder (MWNI) | 102.000 | 1.0% |
| FLV masking | 644.000 | 6.3% |
| Sodium phosphate dibasic anhydrous USP | 280.000 | 2.7% |
| Sodium stearylfumerate NF/EP/JP | 48.600 | 0.5% |

These results showed that it was possible to exceed the taste masking provided by formulation C1 by altering the levels of sucralose, and changing the flavorants. As formulation C1 was believed to be optimal, this change was a surprising improvement.

Example 7: Processing and Manufacture

Figure 6:
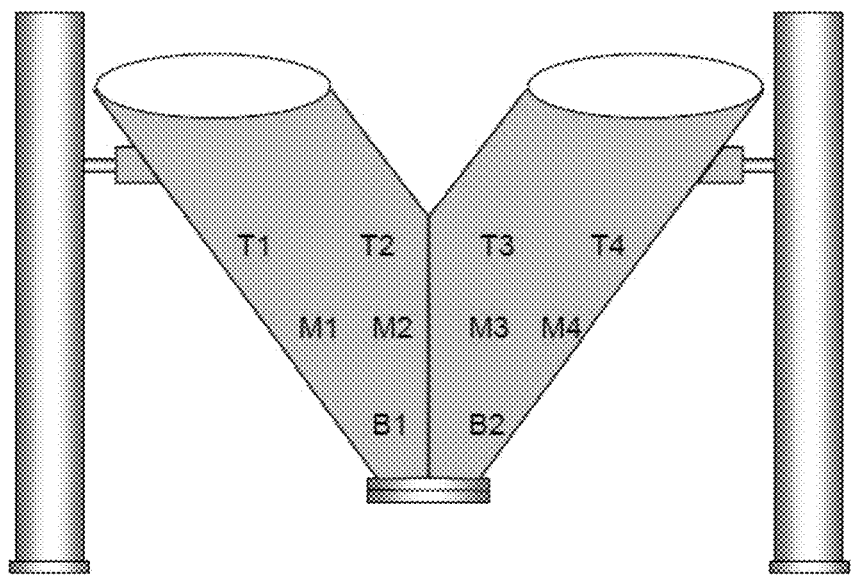
FIG. 6 shows the locations in the 16 Quart V-Shell where blend uniformity samples were obtained.
Figure 7:
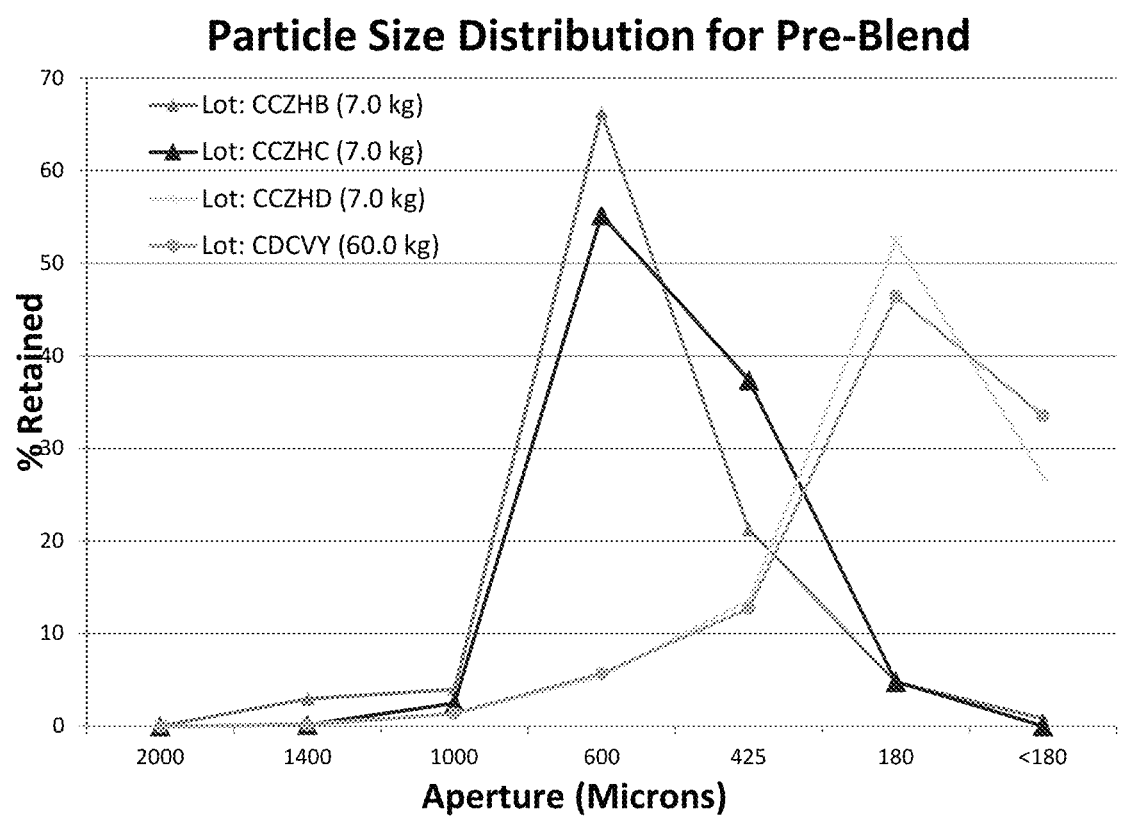
FIG. 7 shows the particle size distribution of the various samples after pre-blending.

Next, several processing steps including pre-blending, compaction, and final blending were subjected to optimization. Blending duration at the pre-blending stage can affect blend uniformity and pre-blend properties for downstream compaction, and was therefore subjected to optimization. Specifically, three separate lots CCZHB, CCZHC, and CCZHD were subjected to various blending times as shown in Table 26. The A&M Blender equipped with a 16 Quart V-Shell, a 197S Quadro Comil with 062R comil screen, and a Gerteis Macro-pactor was used. Blend uniformity, flow index, bulk and tapped density, particle size distribution (PSD), reconstitution time, and dissolution were used as readouts. Blend Uniformity (BU) samples were taken from each batch from the 16 Quart V-Shell from 10 different locations (see FIG. 6). Table 27 summarizes BU results for all three batches. The mean values ranged from 98.1 to 99.8% for PB and 98.1 to 99.3% for TUDCA. The RSD ranged from 0.5 to 1.1% for PB and 1.3 to 1.9 for TUDCA. FIG. 7 is a graph showing the PSD of the samples after pre-blending.

TABLE 26

| Lot # | Blending Time with speed of 25 rpm | Number of rotations |
|---|---|---|
| CCZHB | 15 minutes | 375 revolutions |
| CCZHC | 25 minutes and 48 seconds | 645 revolutions (Mixing duration used in Registration batches) |
| CCZHD | 36 minutes and 36 seconds | 915 revolutions |

TABLE 27

Blend Uniformity Results for Batches CCZHB, CCZHC and CCZHD

| | PERCENTAGE OF API (%) | | | | | |
|---|---|---|---|---|---|---|
| Sample | PB | | | TUDCA | | |
| Location | CCZHB | CCZHC | CCZHD | CCZHB | CCZHC | CCZHD |
| Top 1 | 98.6 | 99.2 | 98.4 | 96.7 | 97.1 | 96.6 |
| Top 2 | 98.2 | 99.7 | 98.0 | 101.1 | 103.4 | 98.2 |
| Top 3 | 97.9 | 100.6 | 100.5 | 97.6 | 99.5 | 101.7 |
| Top 4 | 98.8 | 100.9 | 97.4 | 98.3 | 99.8 | 95.7 |
| Middle 1 | 97.2 | 100.1 | 97.6 | 98.1 | 97.7 | 95.9 |
| Middle 2 | 97.6 | 99.8 | 99.1 | 98.5 | 98.9 | 97.8 |
| Middle 3 | 98.3 | 99.9 | 99.5 | 99.9 | 99.1 | 97.4 |
| Middle 4 | 98.0 | 100.8 | 99.4 | 98.9 | 100.3 | 99.3 |
| Bottom 1 | 98.2 | 98.7 | 99.9 | 97.9 | 99.4 | 99.4 |
| Bottom 2 | 98.5 | 98.7 | 100.0 | 97.9 | 98.2 | 99.0 |
| Mean | 98.1 | 99.8 | 99.0 | 98.5 | 99.3 | 98.1 |
| Minimum | 97.2 | 98.7 | 97.4 | 96.7 | 97.1 | 95.7 |
| Maximum | 98.8 | 100.9 | 100.5 | 101.1 | 103.4 | 101.7 |
| % RSD | 0.5 | 0.8 | 1.1 | 1.3 | 1.7 | 1.9 |

A composite blend sample of 250 g was obtained for physical characterization, including PSD, bulk density, tapped density and flow index. Table 28 shows the physical testing results obtained for all three batches (pre-blend and final blend).

TABLE 28

| | | Pre-Blend | | | | | Final blend | | | | |
|---|---|---|---|---|---|---|---|---|---|---|---|
| | | CCYNH | CCPKP | CCZHB | CCZHC | CCZHD | CCYNH | CCPKP | CCZHB | CCZHC | CCZHD |
| PSD | 10 (2000 µm) | 0 | 0 | 0 | 0 | 0 | 0.06 | 0.06 | 0.07 | 0.18 | 0.18 |
| | 14 (1400 µm) | 0.12 | 0.12 | 2.96 | 0.16 | 0.22 | 17.12 | 14.84 | 15.62 | 22.09 | 19.47 |
| | 18 (1000 µm) | 1.34 | 1.22 | 3.99 | 2.49 | 1.32 | 20.34 | 17.94 | 16.89 | 21.02 | 20.45 |
| | 30 (600 µm) | 6.04 | 5.48 | 66.23 | 55.20 | 5.39 | 19.13 | 16.30 | 18.48 | 19.47 | 18.61 |
| | 40 (425 µm) | 9.88 | 9.65 | 21.24 | 37.35 | 13.63 | 8.42 | 8.82 | 8.79 | 7.85 | 8.01 |
| | 80 (180 µm) | 55.87 | 45.27 | 4.77 | 4.80 | 52.40 | 16.26 | 16.96 | 18.97 | 13.87 | 13.21 |
| | PAN (<180 µm) | 26.75 | 38.26 | 0.81 | 0.00 | 27.04 | 18.67 | 25.08 | 21.18 | 15.52 | 20.07 |
| | Total % | 100.00 | 100.00 | 100.00 | 100.00 | 100.00 | 100.00 | 100.00 | 100.00 | 100.00 | 100.00 |
| | Bulk Density (g/mL) | 0.46 | 0.48 | 0.47 | 0.48 | 0.49 | 0.63 | 0.67 | 0.63 | 0.63 | 0.63 |

TABLE 28-continued

|  | Pre-Blend | | | | | Final blend | | | | |
| --- | --- | --- | --- | --- | --- | --- | --- | --- | --- | --- |
|  | CCYNH | CCPKP | CCZHB | CCZHC | CCZHD | CCYNH | CCPKP | CCZHB | CCZHC | CCZHD |
| Tapped Density (g/mL) | 0.75 | 0.83 | 0.75 | 0.76 | 0.76 | 0.83 | 0.87 | 0.89 | 0.79 | 0.82 |
| Flow Index (mm) | 28 | 26 | 34 | 26 | 26 | 14 | 14 | 9 | 9 | 12 |

Next, the dissolution and reconstitution time of the three batches were analyzed. The results are shown in Tables 29-31.

TABLE 29

Dissolution profile for TUDCA in pre-blending study

| | Time: (minutes) | | | | | |
| --- | --- | --- | --- | --- | --- | --- |
| Batch | 5 | 15 | 30 | 45 | 60 | 75 |
| | Average % Released | | | | | |
| CCZHB | 92 | 96 | 96 | 96 | 96 | 97 |
| CCZHC | 89 | 97 | 98 | 98 | 98 | 98 |
| CCZHD | 92 | 97 | 97 | 97 | 97 | 97 |

TABLE 30

Dissolution profile for PBA in pre-blending study

| | Time: (minutes) | | | | | |
| --- | --- | --- | --- | --- | --- | --- |
| Batch | 5 | 15 | 30 | 45 | 60 | 75 |
| | Average % Released | | | | | |
| CCZHB | 94 | 97 | 97 | 97 | 97 | 97 |
| CCZHC | 91 | 99 | 99 | 99 | 100 | 100 |
| CCZHD | 93 | 98 | 98 | 98 | 98 | 98 |

TABLE 31

Reconstitution time for Batch CCZHB, CCZHC and CCZHD

| Batch | Time (minutes:seconds) |
| --- | --- |
| CCZHB | 13:04 |
| CCZHC | 11:03 |
| CCZHD | 11:57 |

No statistical significance was observed in the blend uniformity, dissolution or reconstitution time for the three batches. However, significant differences were observed in the PSD of the three batches after pre-blending. The pre-blend PSD for CCZHB and CCZHC, which were subjected to a shorter blending time, indicated coarser materials. This suggests that increased blending time results in more particle attrition. A shorter pre-blending time is therefore preferred.

In the compaction step, several compaction parameters such as roller gap, compaction force and granulation screen size are likely to impact the physical properties of the final granules, and the extent and rate of drug release. These factors were therefore subjected to optimization, and their effects on dissolution, physical properties, and reconstitution time were evaluated. Compaction speed is an additional factor that could impact physical properties and was evaluated along during the final blending study. A bulk blend (Lot CDCVY), pre-blended based on the optimal pre-blending parameters determined above was divided into twelve sub-batches, and roller compaction and granulation of each sub-batch was carried out using a set of different parameters for compaction force (5-15 kN/cm), roller gap (2-3 mm) and graduation screen size (1-2 mm) (Table 32). Physical properties, dissolution and reconstitution time on the final blend were evaluated for each sub-batch. Tables 33 and 34 show physical testing results obtained for all 12 sub-batches.

TABLE 32

Roller compaction and granulation parameters

| Trial # | Screen (mm) | Gap (mm) | Force (KN/cm) |
| --- | --- | --- | --- |
| 1 | 1 | 3 | 15 |
| 2 | 1 | 3 | 5 |
| 3 | 1.5 | 2.5 | 10 |
| 4 | 2 | 3 | 15 |
| 5 | 2 | 3 | 5 |
| 6 | 1.5 | 2.5 | 10 |
| 7 | 1 | 2 | 15 |
| 8 | 1 | 2 | 5 |
| 9 | 1.5 | 2.5 | 10 |
| 10 | 2 | 2 | 5 |
| 11 | 2 | 2 | 15 |
| 12 | 1.5 | 2.5 | 10 |

TABLE 33

Sub-batches 1-6

| | | Final blend | | | | | |
| --- | --- | --- | --- | --- | --- | --- | --- |
| | TEST | Sub-batch #1 | Sub-batch #2 | Sub-batch #3 | Sub-batch #4 | Sub-batch #5 | Sub-batch #6 |
| PSD | 10 (2000 µm) | 0.05 | 0.03 | 0.04 | 0.28 | 0.12 | 0.04 |
| | 14 (1400 µm) | 0.11 | 0.26 | 2.21 | 28.33 | 13.00 | 1.99 |
| | 18 (1000 µm) | 0.86 | 0.51 | 21.85 | 24.62 | 17.38 | 22.97 |
| | 30 (600 µm) | 25.38 | 22.48 | 24.46 | 17.96 | 16.80 | 24.70 |
| | 40 (425 µm) | 17.01 | 15.02 | 10.68 | 7.20 | 8.58 | 10.38 |

TABLE 33-continued

Sub-batches 1-6

| | Final blend | | | | | |
|---|---|---|---|---|---|---|
| TEST | Sub-batch #1 | Sub-batch #2 | Sub-batch #3 | Sub-batch #4 | Sub-batch #5 | Sub-batch #6 |
| 80 (180 μm) | 30.08 | 30.90 | 19.70 | 11.10 | 20.66 | 19.53 |
| PAN (<180 μm) | 26.51 | 30.80 | 21.06 | 10.51 | 23.46 | 20.39 |
| Total % | 100.00 | 100.00 | 100.00 | 100.00 | 100.00 | 100.00 |
| Bulk Density (g/mL) | 0.62 | 0.57 | 0.63 | 0.63 | 0.60 | 0.63 |
| Tapped Density (g/mL) | 0.82 | 0.81 | 0.80 | 0.80 | 0.79 | 0.81 |
| Flow Index (mm) | 9 | 14 | 8 | 9 | 12 | 9 |

TABLE 34

Sub-batches 7-12

| | | Pre-Blend | | | Final blend | | |
|---|---|---|---|---|---|---|---|
| TEST | | Sub-batch #7 | Sub-batch #8 | Sub-batch #9 | Sub-batch #10 | Sub-batch #11 | Sub-batch #12 |
| PSD | 10 (2000 μm) | 0.06 | 0.10 | 0.14 | 0.17 | 0.46 | 0.14 |
| | 14 (1400 μm) | 0.22 | 0.28 | 2.00 | 17.60 | 27.58 | 2.53 |
| | 18 (1000 μm) | 0.92 | 0.79 | 21.13 | 19.08 | 22.83 | 24.26 |
| | 30 (600 μm) | 28.94 | 25.98 | 23.37 | 17.11 | 17.82 | 25.65 |
| | 40 (425 μm) | 17.16 | 15.30 | 10.85 | 8.29 | 7.85 | 10.68 |
| | 80 (180 μm) | 28.96 | 30.15 | 20.95 | 19.84 | 13.34 | 18.98 |
| | PAN (<180 μm) | 23.74 | 27.40 | 21.56 | 17.91 | 10.12 | 17.76 |
| Total % | | 100.00 | 100.00 | 100.00 | 100.00 | 100.00 | 100.00 |
| Bulk Density (g/mL) | | 0.64 | 0.59 | 0.61 | 0.60 | 0.61 | 0.62 |
| Tapped Density (g/mL) | | 0.82 | 0.81 | 0.77 | 0.78 | 0.78 | 0.79 |
| Flow Index (mm) | | 9 | 12 | 9 | 14 | 9 | 9 |

Figure 8:
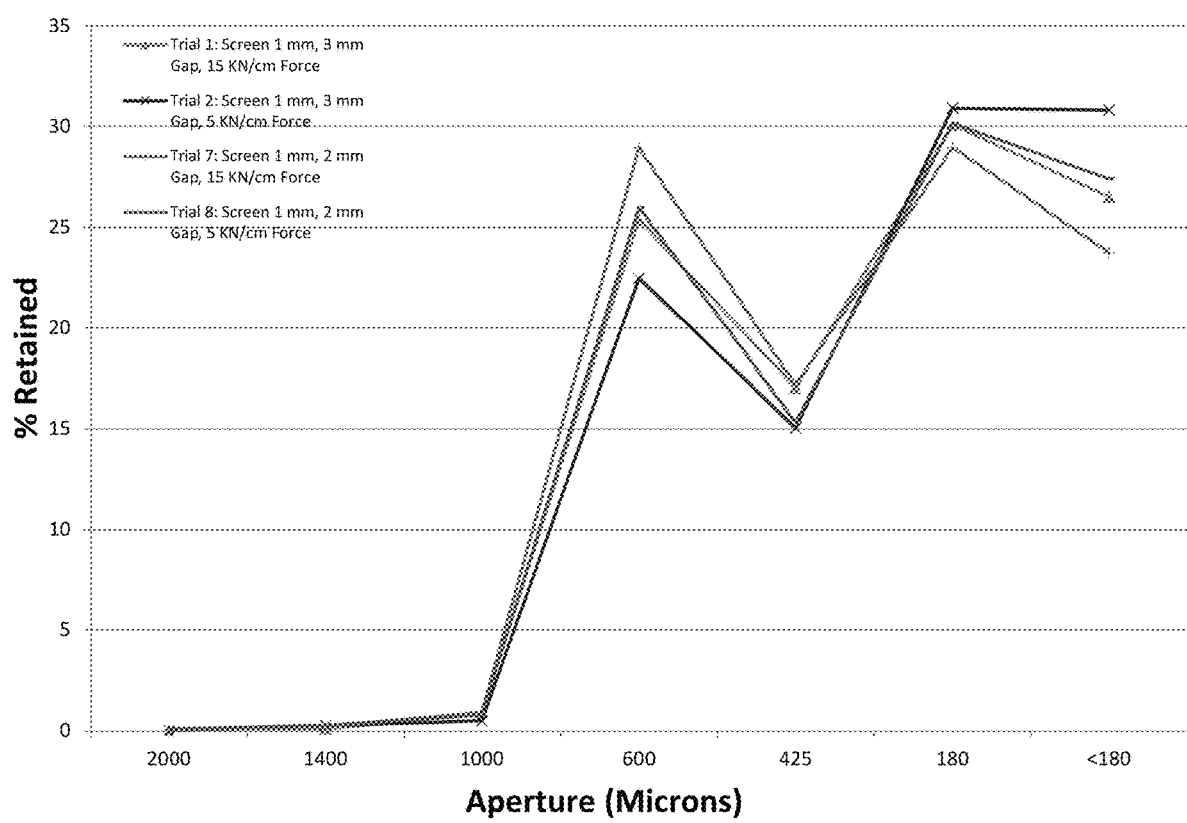
FIG. 8 shows the particle size distribution of the various samples after granulation with a screen size of 1.0 mm.
Figure 9:
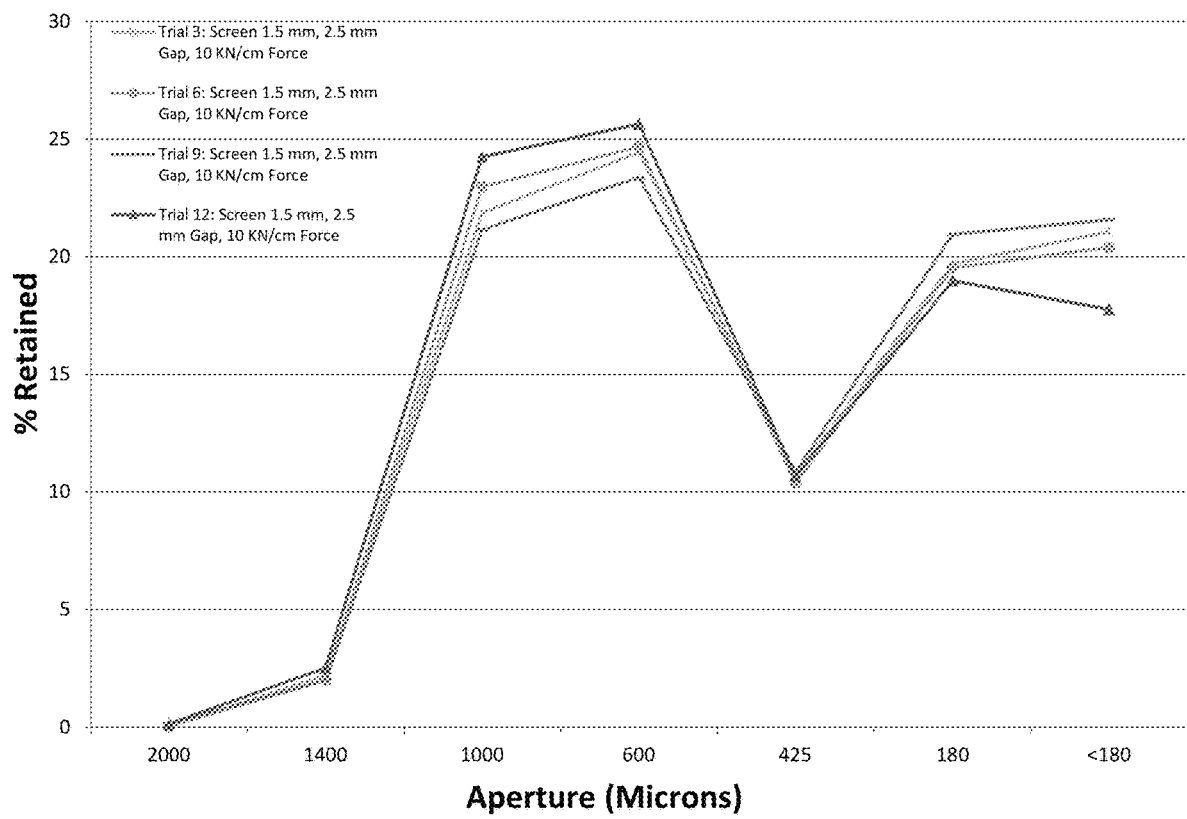
FIG. 9 shows the particle size distribution of the various samples after granulation with a screen size of 1.5 mm.
Figure 10:
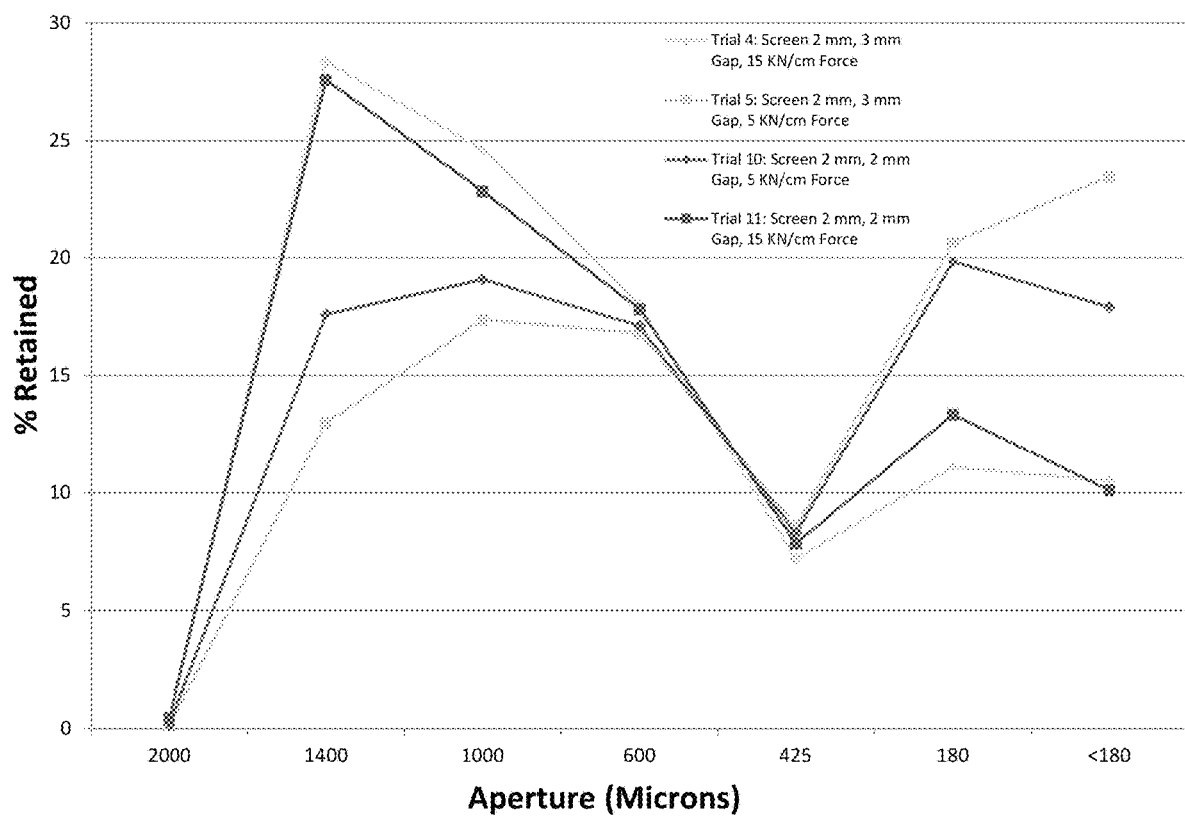
FIG. 10 shows the particle size distribution of the various samples after granulation with a screen size of 2.0 mm.
Figure 11:
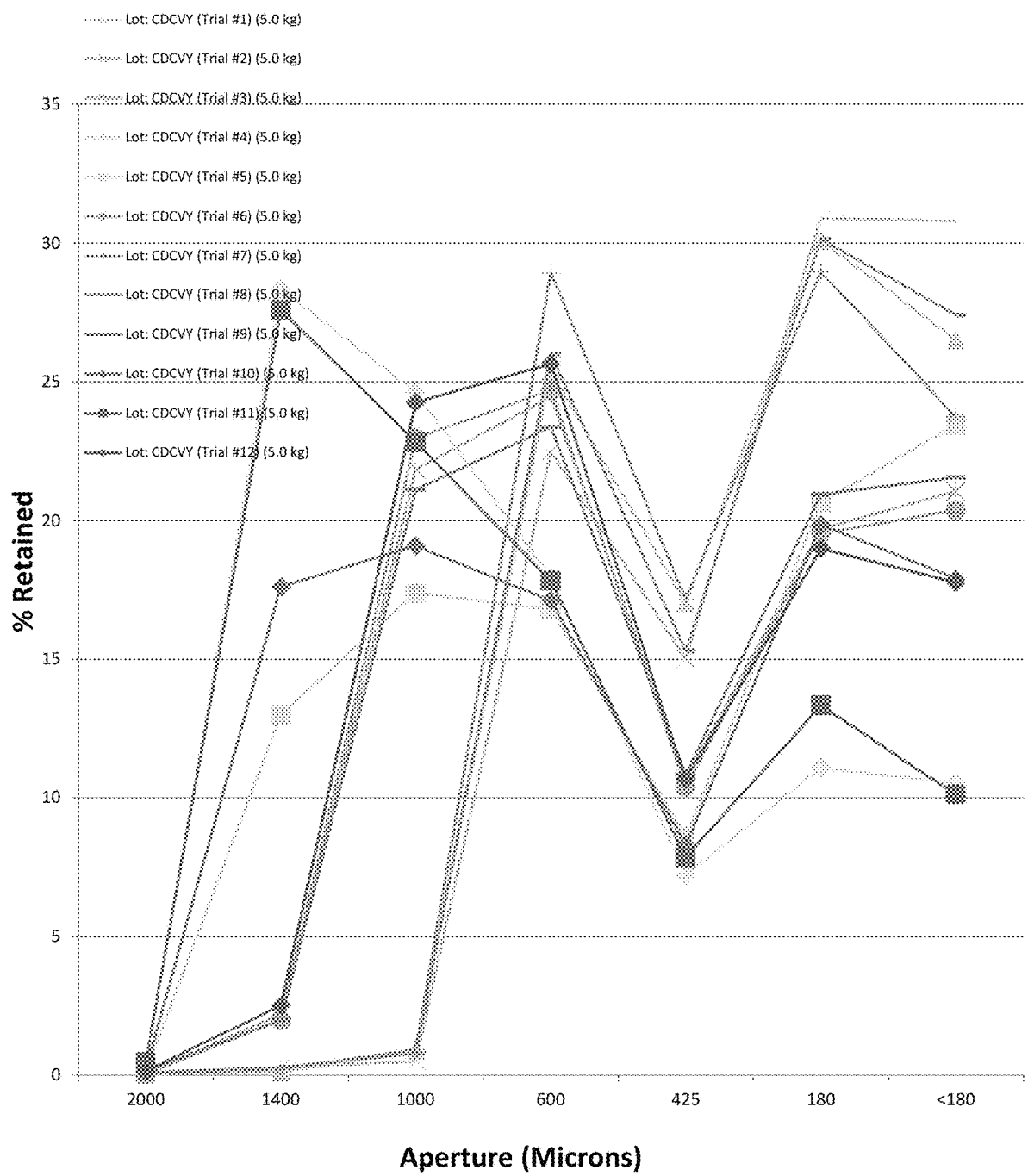
FIG. 11 shows the combined results from FIGS. 8-10.

FIGS. 8-10 show particle size distribution under granulation screen sizes of 1.00 mm, 1.5 mm, and 2.0 mm, respectively; the combined results are shown in FIG. 11.

The above physical characterization data was entered into Minitab v. 18 statistical program and the statistical model was used to determine the optimal compaction parameters based on the below set of response targets. The response target in regards to particle size distribution was selected to achieve a narrow PSD for downstream packaging activities.

TABLE 35

| Response | Target |
|---|---|
| Particle Size Distribution | |
| Material > 1400 μm | NMT 10% |
| 425 μm < Material < 1400 μm | 45% ≤ Material ≤ 65% |
| Material < 425 μm | NMT 45% |
| Reconstitution Time | NMT 15 minutes |
| TUDCA Dissolution | Q = 75% → individual values NLT 85% @ 15 minutes |
| PB Dissolution | Q = 75% → individual values NLT 85% @ 15 minutes |

Based on the statistical analysis, significant differences were observed in the PSD for all twelve sub-batches in the final blend. Bulk density and flow index showed moderately significant differences in the overall statistical analysis. The results from tapped density showed no significant difference. As physical characteristics of the final blend are important factors for downstream packaging, a homogeneous particle size distribution is preferred. In order to achieve the above response targets, the optimal compaction parameters for the predicted model was considered to be a roller gap width of about 2 mm to about 3 mm, a compaction force of about 5-15 kN/cm (target: 10.0 kN/cm) and a granulation screen size of about 1.5 mm.

Reconstitution Time and Dissolution Profile

Figure 12:
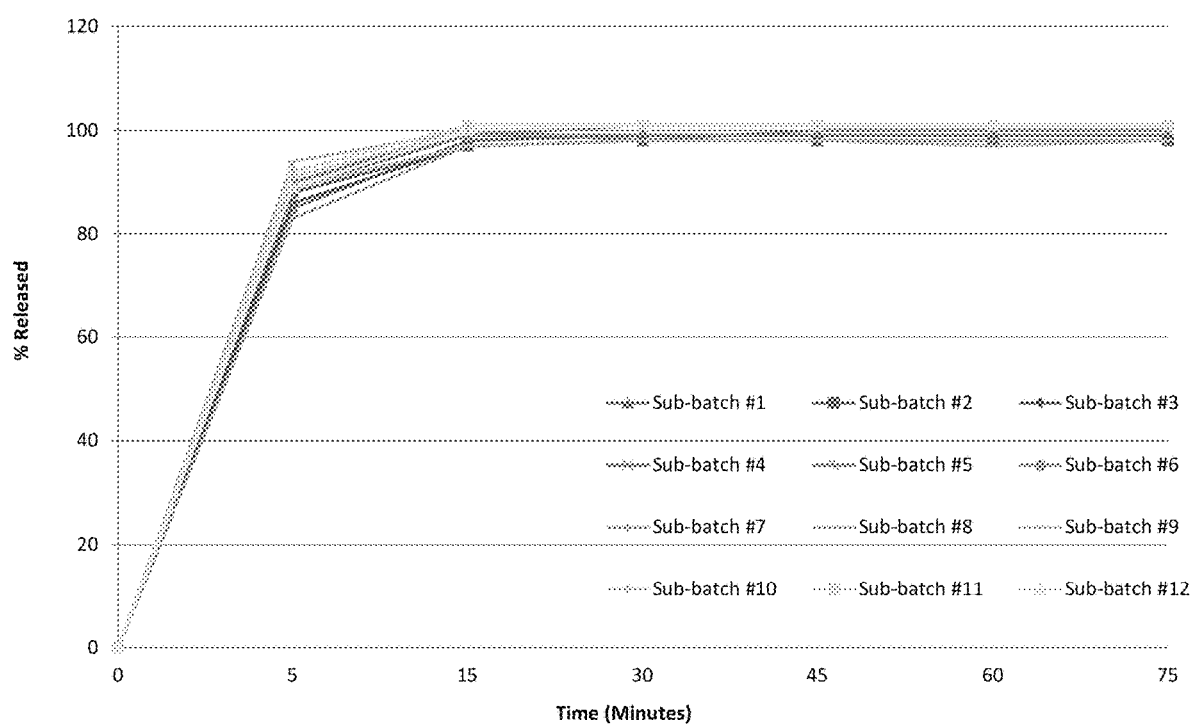
FIG. 12 is a graph showing the dissolution profiles of TUDCA in the various sub-batches.
Figure 13:
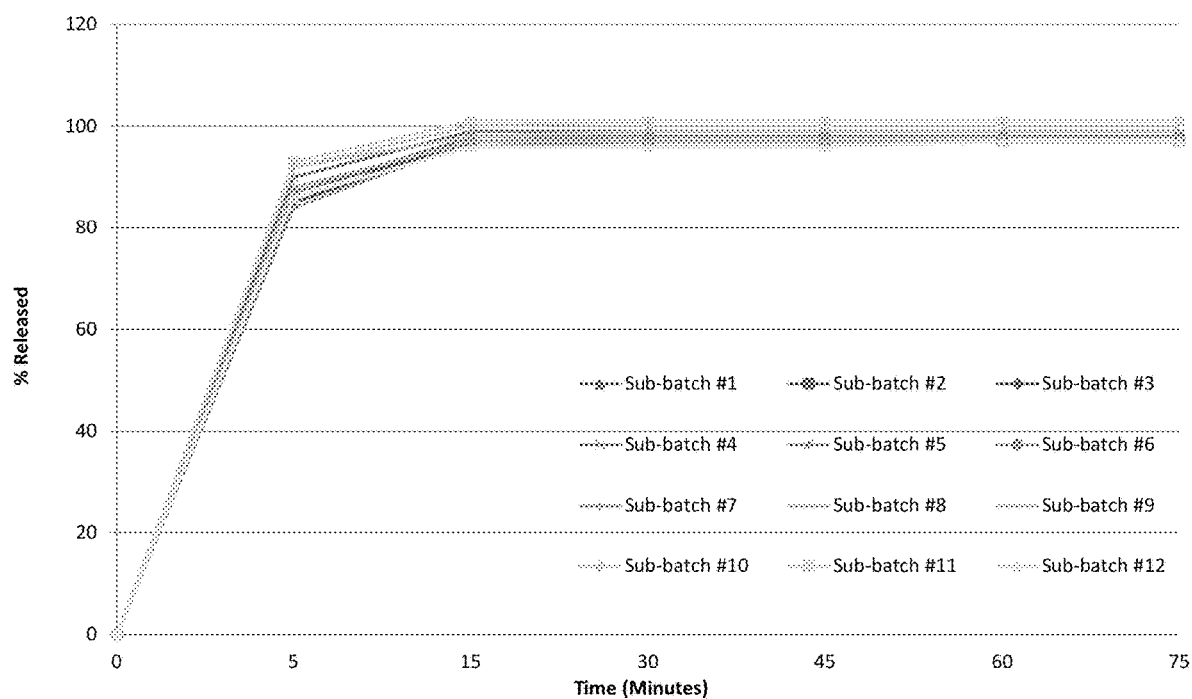
FIG. 13 is a graph showing the dissolution profiles of sodium phenylbutyrate in the various sub-batches.

Since the compaction process can impact the physical properties of the granules and thus the extent and rate of drug release, reconstitution time and dissolution profile were further evaluated. Tables 36-38 list the reconstitution time and mean dissolution profile for the twelve sub-batches. The dissolution profiles of TUDCA and sodium phenylbutyrate in each of the sub-batches are shown in FIGS. 12 and 13 respectively.

TABLE 36

Reconstitution time

| Sub-Batch | Time: (minutes:seconds) |
|---|---|
| #1 | 9:14 |
| #2 | 8:30 |
| #3 | 10:23 |
| #4 | 13:19 |
| #5 | 10:56 |
| #6 | 12:06 |
| #7 | 13:12 |
| #8 | 9:27 |
| #9 | 13:09 |
| #10 | 13:57 |

TABLE 36-continued

Reconstitution time

| Sub-Batch | Time: (minutes:seconds) |
|---|---|
| #11 | 16:31 |
| #12 | 13:26 |

TABLE 37

Dissolution Profile for TUDCA

| Sub-batch | \multicolumn{6}{c}{Time: (minutes) % Released} |
|---|---|---|---|---|---|---|
|  | 5 | 15 | 30 | 45 | 60 | 75 |
| #1 | 85 | 98 | 99 | 99 | 99 | 99 |
| #2 | 88 | 97 | 98 | 98 | 98 | 98 |
| #3 | 86 | 97 | 98 | 98 | 98 | 98 |
| #4 | 89 | 99 | 99 | 99 | 99 | 99 |
| #5 | 90 | 100 | 98 | 100 | 100 | 100 |
| #6 | 90 | 99 | 101 | 101 | 101 | 101 |
| #7 | 83 | 97 | 98 | 98 | 98 | 98 |
| #8 | 89 | 97 | 98 | 98 | 97 | 98 |
| #9 | 94 | 100 | 101 | 101 | 101 | 101 |
| #10 | 91 | 100 | 101 | 101 | 101 | 101 |
| #11 | 92 | 101 | 101 | 101 | 101 | 101 |
| #12 | 89 | 100 | 101 | 101 | 101 | 101 |

TABLE 38

Dissolution Profile for PB

| Sub-batch | \multicolumn{6}{c}{Time: (minutes) % Released} |
|---|---|---|---|---|---|---|
|  | 5 | 15 | 30 | 45 | 60 | 75 |
| #1 | 85 | 98 | 98 | 98 | 98 | 98 |
| #2 | 87 | 97 | 97 | 97 | 97 | 97 |
| #3 | 85 | 97 | 97 | 97 | 97 | 97 |
| #4 | 90 | 99 | 99 | 99 | 99 | 99 |
| #5 | 86 | 96 | 97 | 97 | 97 | 97 |
| #6 | 87 | 98 | 98 | 98 | 98 | 98 |
| #7 | 84 | 97 | 98 | 98 | 98 | 98 |
| #8 | 88 | 97 | 97 | 97 | 97 | 97 |
| #9 | 92 | 98 | 99 | 99 | 99 | 99 |
| #10 | 92 | 100 | 101 | 101 | 101 | 101 |
| #11 | 93 | 101 | 101 | 101 | 101 | 101 |
| #12 | 86 | 96 | 96 | 96 | 97 | 97 |

Moderately significant differences in the reconstitution time were observed among the different sub-batches. All twelve sub-batches met the bulk product specification of NMT (no more than) 20 minutes. In order to establish a more sensitive limit, a reconstitution time of NMT=15 minutes was entered into the statistical program as a response target. With this response target, no significant differences were observed among the sub-batches, except for sub-batch #11, which had the longest reconstitution time of about 16 to 17 minutes.

The dissolution profiles were not strongly influenced by the parameters tested. TUDCA dissolution % release and PB dissolution % release both appeared to be complete after 15 minutes. The dissolution % release results were well above the target limit of Q=75% @ 15 minutes. FIGS. 12 and 13 show dissolution profiles of the sub-batches.

To evaluate whether a lower temperature could impact the physical properties of the granules, a cooling unit at a temperature of 15±2° C. was added to the roller compactor. Reduced clumping and agglomeration was observed from addition of the cooling unit.

Final Blending Optimization

Figure 14:
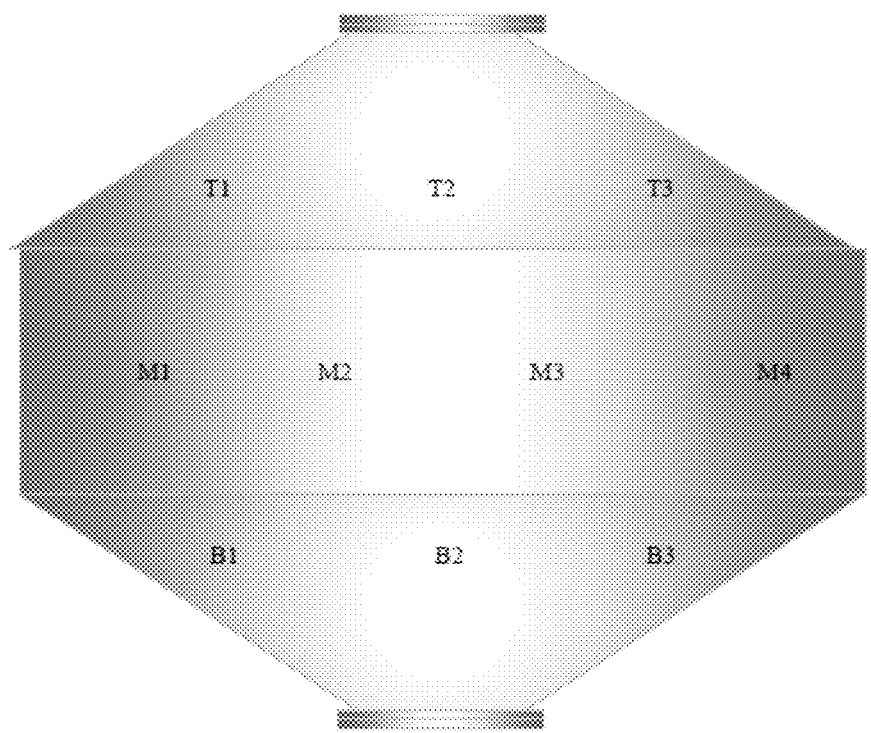
FIG. 14 shows the locations where blend uniformity samples were obtained for the final blending analysis.

Blending time during the final blending step could affect blend uniformity and final blend physical properties that are critical for downstream packaging, and was therefore subjected to optimization. Table 39 shows the varying duration and the corresponding number of revolutions used. Blend uniformity and physical characterization were evaluated. BU samples were obtained from the locations shown in FIG. 14. The BU results are shown in Tables 40-42.

TABLE 39

| Level | Blending time with fixed speed 20.5 rpm | Number of revolutions |
|---|---|---|
| 1 | 0 minutes | 0 revolutions |
| 2 | 3 minutes | 61.5 revolutions (Similar mixing duration used in Registration batches which was 60 revolutions) |
| 3 | 5 minutes | 102.5 revolutions |

TABLE 40

Batch CDCWH Pre-blend

| Sample Location | % PBA | % TUDCA |
|---|---|---|
| Top 1 | 100.1 | 92.7 |
| Top 2 | 100.3 | 98.8 |
| Top 3 | 99.3 | 100.9 |
| Middle 1 | 98.7 | 97.3 |
| Middle 2 | 100.0 | 101.3 |
| Middle 3 | 98.5 | 98.1 |
| Middle 4 | 101.1 | 98.2 |
| Bottom 1 | 98.9 | 98.8 |
| Bottom 2 | 98.0 | 99.6 |
| Bottom 3 | 99.6 | 98.9 |
| Mean | 99.5 | 98.5 |
| Min. | 98.0 | 92.7 |
| Max | 101.1 | 101.3 |
| % RSD | 1.0 | 2.4 |

Adequate pre-blend homogeneity was achieved, with mean values of 99.5% for PB, 98% for TUDCA, and % RSD values being less than 2.5% for both active pharmaceutical ingredients.

TABLE 41

Batch CDCWH compacted granules

| Sample Location | % PBA | | % TUDCA | |
|---|---|---|---|---|
|  | Container #1 | Container #2 | Container #1 | Container #2 |
| Top | 94.5 | 96.0 | 96.7 | 98.5 |
| Middle | 95.5 | 95.2 | 97.3 | 99.2 |
| Bottom | 98.0 | 94.0 | 97.0 | 98.2 |
| Mean | 96.0 | 95.1 | 97.0 | 98.2 |
| Minimum | 94.5 | 94.0 | 96.7 | 98.2 |
| Maximum | 98.0 | 96.0 | 97.3 | 99.2 |
| % RSD | 1.9 | 1.1 | 0.3 | 0.5 |
| Overall Mean | 95.5 | | 97.8 | |
| Overall Min. | 94.0 | | 96.7 | |
| Overall Max. | 98.0 | | 99.2 | |
| Overall RSD | 1.5 | | 1.0 | |

Adequate homogeneity was also achieved after roller compaction, with an overall mean value of 95.5% for PB, 97.8% for TUDCA, and % RSD values being less than 2.0% for both active pharmaceutical ingredients.

TABLE 42

Batch CDCWH final blend

| Sample Location | % PBA | | | % TUDCA | | |
|---|---|---|---|---|---|---|
| | No Blending | 3 minutes blending | 5 minutes blending | No Blending | 3 minutes blending | 5 minutes blending |
| Top 1 | 98.3 | 100.6 | 95.8 | 100.0 | 96.9 | 96.9 |
| Top 2 | 103.6 | 98.6 | 101.6 | 99.8 | 96.9 | 99.4 |
| Top 3 | 98.8 | 99.2 | 100.0 | 99.5 | 98.9 | 97.6 |
| Top 4 | 99.6 | 101.3 | 99.9 | 97.9 | 99.4 | 98.5 |
| Middle 1 | 101.3 | 99.7 | 98.7 | 98.3 | 98.8 | 98.7 |
| Middle 2 | 95.4 | 96.3 | 99.2 | 98.4 | 94.2 | 96.7 |
| Middle 3 | 100.4 | 99.3 | 98.4 | 99.1 | 98.2 | 96.2 |
| Middle 4 | 100.5 | 98.8 | 102.4 | 98.6 | 97.3 | 98.0 |
| Bottom 1 | 94.0 | 100.2 | 101.1 | 95.4 | 97.8 | 98.6 |
| Bottom 2 | 98.5 | 99.3 | 99.2 | 98.3 | 97.8 | 99.0 |
| Mean | 99.0 | 99.3 | 99.6 | 98.5 | 97.6 | 98.0 |
| Minimum | 94.0 | 96.3 | 95.8 | 95.4 | 94.2 | 96.2 |
| Maximum | 103.6 | 101.3 | 102.4 | 100.0 | 99.4 | 99.4 |
| % RSD | 2.8 | 1.3 | 1.9 | 1.3 | 1.5 | 1.1 |

No significant difference in blend uniformity was observed with different final blending durations. Adequate final blend homogeneity was achieved; with mean values ranging from 99.0 to 99.6% for PBA and 97.6 to 98.5% for TUDCA. The % RSD ranged from 1.3 to 2.8% for PBA and 1.1 to 1.5 for TUDCA. Higher variation in the BU results was observed when no final blending was performed, as compared to blending for either 3 or 5 minutes, though the individual value at each location was well within the recommended range of 85%-115% for blend uniformity.

A composite blend sample of 250 g was obtained for physical characterization. Table 43 lists the physical testing results. There was no significant differences in the PSD, or the bulk and tapped density; however, there was a significant difference in the flow index. Improved flow index was observed under the no blending condition. Shorter blending time also resulted in coarser materials. Therefore no final blending was determined to be the preferred condition.

TABLE 43

Physical characterization Batch CDCWH

| Test | | Final Blend | | |
|---|---|---|---|---|
| | | No Blending | 3 minutes blending | 5 minutes blending |
| PSD (%) | 10 (2000 µm) | 0 | 0 | 0 |
| | 14 (1400 µm) | 1.16 | 1.34 | 1.30 |
| | 18 (1000 µm) | 18.31 | 17.70 | 17.08 |
| | 30 (600 µm) | 23.73 | 22.18 | 22.14 |
| | 40 (425 µm) | 11.59 | 10.43 | 10.53 |
| | 80 (180 µm) | 21.38 | 20.40 | 21.07 |
| | PAN (<180 µm) | 23.83 | 27.95 | 27.88 |
| | Total | 100.00 | 100.00 | 100.00 |
| Bulk Density (g/mL) | | 0.60 | 0.62 | 0.63 |
| Tapped Density (g/mL) | | 0.82 | 0.83 | 0.85 |
| Flow Index (mm) | | 9 | 16 | 14 |

TABLE 44

PSD Batch CDCWH

| Particle Size Distribution | Target | No Blending | 3 minutes blending | 5 minutes blending |
|---|---|---|---|---|
| Material > 1400 µm | NMT 10% | 1.16 | 1.34 | 1.30 |
| 425 µm < Material < 1400 µm | 45% ≤ Material ≤ 65% | 53.63 | 50.31 | 49.75 |
| Material < 425 µm | NMT 45% | 45.21 | 48.38 | 48.95 |

Dissolution and Reconstitution Time

No statistical significance in dissolution or reconstitution was observed (Tables 45-47). Table 48 shows a preferred set of physical characteristics for the bulk product.

TABLE 45

Dissolution profile for TUDCA (Batch CDCWH)

| Blending Time | Time: (minutes) | | | | | |
|---|---|---|---|---|---|---|
| | 5 | 15 | 30 | 45 | 60 | 75 |
| | Average % Released | | | | | |
| No Blending | 89 | 96 | 96 | 96 | 96 | 96 |
| 3 minutes blending | 90 | 97 | 97 | 97 | 97 | 97 |
| 5 minutes blending | 87 | 95 | 96 | 96 | 96 | 95 |

TABLE 46

Dissolution profile for PBA (Batch CDCWH)

| Time Blending | Time: (minutes) | | | | | |
|---|---|---|---|---|---|---|
| | 5 | 15 | 30 | 45 | 60 | 75 |
| | Average % Released | | | | | |
| No Blending | 90 | 95 | 95 | 95 | 95 | 95 |
| 3 minutes blending | 93 | 98 | 98 | 98 | 98 | 98 |
| 5 minutes blending | 90 | 98 | 98 | 98 | 98 | 98 |

TABLE 47

Reconstitution time (Batch CDCWH)

| Blending time | Time (minutes) |
|---|---|
| No Blending | 16 |
| 3 minutes blending | 15 |
| 5 minutes blending | 15 |

TABLE 48

| Particle Size Distribution | Target |
|---|---|
| Material > 1400 μm | *NMT 10% |
| 425 μm < Material < 1400 μm | 45% ≤ Material ≤ 65% |
| Material < 425 μm | NMT 50% |
| Bulk Density | 0.5-0.7 g/mL |
| Tapped Density | 0.7-0.9 g/mL |
| Flow Index | **NLT 16 mm |

*NMT: Not More Than
**NLT: Not Less Than

The above optimization studies revealed preferred processing conditions to achieve improved flow properties and reduced levels of fine particles in the final product, which are thought to be detrimental to flow. It was determined that: i. a pre-blending time corresponding to about 375 revolutions, ii. a compaction force of between 5-15 kN/cm, gap width of between about 1.0 mm to about 5.0 mm, roller speed of about 4 to about 12 rpm, and granulation screen size of about 1.5 mm, and iii. no final blending, resulted in improved product properties including flowability. Together these improvements resulted in a Carr's Index of approximately 8-9, a significant and surprising improvement from the original formulation developed (~20 Carr Index).

Statistical Analysis

The results from the compaction study was subjected to statistical analysis. The input settings were as follows:

| Factor | Minimum | Center | Maximum |
|---|---|---|---|
| Screen Size (mm) | 1.0 | 1.5 | 2.0 |
| Gap Width (mm) | 2.0 | 2.5 | 3.0 |
| Press Force (kN/cm) | 5.0 | 10.0 | 15.0 |

The following physical responses were analyzed: % Retained on 10 mesh, % Retained on 14 mesh, % Retained on 18 mesh, % Retained on 30 mesh, % Retained on 40 mesh, % Retained on 80 mesh, % Pan, Bulk Density, Tapped Density, and Flow Index.

Results—Particle Size Distribution Responses

Good or very good models were found for each of the particle size distribution responses (% Retained on 10 mesh, % Retained on 14 mesh, % Retained on 18 mesh, % Retained on 30 mesh, % Retained on 40 mesh, % Retained on 80 mesh, and % Pan).

The main effects of Screen Size and Press Force, and the Screen Force interaction effect were statistically significant with ≥95% confidence in each of these models. The curvature effect was also significant in each of the PSD response models except % Retained on 10 mesh and % Pan. The presence of the curvature term in a model indicates that at least one of the main factors has a quadratic effect on the responses. The Gap Width main effect was statistically significant with ≥95% confidence in the models for % Retained on 30 mesh and for % Pan.

The model coefficient for Screen Size was positive in the models for % Retained on 10 mesh, % Retained on 14 mesh, and % Retained on 18 mesh, while the coefficient is negative in the models for % Retained on 30 mesh, % Retained on 40 mesh, % Retained on 80 mesh, and % Pan. This indicates that increasing the Screen Size tends to increase the amount of larger particles and decrease the amount of smaller particles in the compacted blend.

Similarly, the model coefficient for Press Force was positive in the models for % Retained on 10 mesh, % Retained on 14 mesh, % Retained on 18 mesh, % Retained on 30 mesh, and % Retained on 40 mesh, while the coefficient is negative in the models for % Retained on 80 mesh and % Pan. This indicates that increasing the Press Force also tends to increase the amount of larger particles and decrease the amount of smaller particles in the compacted blend.

The model coefficient for Gap Width was negative for % Retained on 10 mesh and % Retained on 30 mesh. It was approximately equal to zero for % Retained on 14 mesh, % Retained on 18 mesh, % Retained on 40 mesh, and % Retained on 80 mesh. The Gap Width coefficient is positive for % Pan. Therefore, increasing Gap Width may decrease the amount of larger particles and increase the amount of smaller particles in the compacted blend.

Good predictive models were also found for the Bulk Density and Flow Index.

Example 8: Forced Degradation Studies

Each API and the final formulation (referred to as "AMX powder in sachet") containing both APIs were also subjected to forced degradation studies. The study included stressing samples of PB (sodium phenylbutyrate) API, TURSO API, placebo, and AMX Powder in Sachet under thermal, thermal-humidity, light, oxidation, acid, or base conditions (Table 49).

TABLE 49

| | | | % Degradation Observed | | |
|---|---|---|---|---|---|
| Samples | Stress Condition | Stress Condition Details | PB API | TURSO API | AMX Powder in Sachet |
| PB API (4500 mg/sample), TURSO API (1500 mg/sample), Placebo mixture, and AMX Powder in Sachet | Thermal | 85° C. for 10 days | None | None | PB: ~8% TURSO: ~19% |
| | Thermal-Humidity | 85° C. + 1.0 mL water per sample for 10 days | None | 100% | PB: ~4% TURSO: ~10% |
| | Oxidation | 10 mL of 3% $H_2O_2$ per sample | None | 3% | PB: None TURSO: ~2% |
| | Acid | 10 mL of 1.0N HCl per | None | None | None |

TABLE 49-continued

| Samples | Stress Condition | Stress Condition Details | % Degradation Observed | | |
|---|---|---|---|---|---|
| | | | PB API | TURSO API | AMX Powder in Sachet |
| (4500 mg PB and 1500 mg TURSO per sample) | | sample for 3 days at 50° C. 10 mL of 1.0N HCl per sample for 7 days at 50° C. | None | ~3% | None |
| | Base | 10 mL of 1.0N NaOH per sample for 3 days at 50° C. | None | ~5% | None |
| | | 10 mL of 1.0N NaOH per sample for 7 days at 50° C. | None | ~17% | None |
| | Light | 1 × ICH condition (White light NLT 1.2 million lux hours and UV light NLT 200 W hours/m²) | None | None | None |

The assay results of the control and stress sample are summarized in Table 50. The Relative Mass Balance Deficit values are listed in Table 51.

The PB API did not degrade in any of the forced degradation conditions studied. The TURSO API did not degrade in thermal and light conditions. It degraded slightly in acidic condition by Day 7 and in oxidation and base condition by Day 3. By Day 7, TURSO API degraded by ~17% in base condition. The TURSO API in Thermal-Humidity condition completely changed in nature or precipitated in solution as no TURSO peak was detected in the assay sample solution. The exposure of placebo mixture to forced degradation conditions did not generate any peaks that interfered at the retention times of active peaks.

The PB and TURSO in AMX Powder in Sachet did not degrade in acid, base, and light conditions. PB in sachet did not degrade in oxidation condition, but degraded by approximately 8% and 4% in Thermal and Thermal-Humidity condition, respectively. TURSO in sachet slightly degraded in oxidation condition and by 19% and 10% in Thermal and Thermal-Humidity condition, respectively. Furthermore, surprisingly, the extent of TURSO degradation in Thermal-Humidity condition was much lower in sachet compared to full degradation in TURSO API sample.

TABLE 50

| Sample | Results | Control | Thermal | Thermal-Humidity | Oxidation | Acid 3 Days |
|---|---|---|---|---|---|---|
| PB API | % PB | 99.2 | 98.9 | 99.3 | 98.8 | 99.1 |
| | % PB remaining | | 99.7 | 100.1 | 99.4 | 99.9 |
| | PR Peak Purity | Pass | Pass | Pass | Pass | Pass |
| | Conclusion | | No significant Degradation | No significant Degradation | No significant Degradation | No significant Degradation |
| TUDCA API | % TUDCA | 100.2 | 100.6 | TUDCA Peak was not detected Solution appeared cloudy/white.* | 97.1 | 100.0 |
| | % TUDCA remaining | | 100.4 | 0% | 93.9 | 99.8 |
| | TUDCA Peak Purity | Fail | Fail | N/A (no peak) | Fail | Fail |
| | Conclusion | | No significant Degradation | Full degradation/ sample precipitation may have occurred | ~3% degradation | No significant Degradation |
| Placebo | % PB | ND | ND | ND | ND | ND |
| | % TUDCA | ND | ND | ND | ND | ND |
| | Conclusion | | Causes no interference at retention time of actives | Causes no interference at retention time of actives | Causes no interference at retention time of actives | Causes no interference at retention time of actives |
| AMX-0035 Powder in Sachet | % PB | 99.1 | 90.8 | 94.7 | 98.5 | 98.9 |
| | % TUDCA | 97.2 | 78.4 | 87.1 | 95.2 | 96.1 |
| | % PB remaining | | 91.6 | 95.6 | 99.4 | 99.8 |
| | % TUDCA remaining | | 80.7 | 89.6 | 97.9 | 98.9 |
| | PB Peak Purity | Pass | Pass | Pass | Pass | Pass |
| | TUDCA Peak Purity | Fail | Fail | Fail | Fail | Fail |
| | Conclusion | | ~8% PB and ~19% TUDCA degradation | ~4% PB and ~10% TUDCA degradation | PB-No significant degradation, TUDCA- ~2% | No significant Degradation |

TABLE 50-continued

| Sample | Results | Base 3 Days | Acid 7 Days | Base 7 Days | Light Control | Light |
|---|---|---|---|---|---|---|
| PB API | % PB | 99.9 | 99.7 | 99.8 | 99.0 | 98.3 |
| | % PB remaining | 99.7 | 100.5 | 100.6 | | 99.3 |
| | PR Peak Purity | Pass | Pass | Pass | Pass | Pass |
| | Conclusion | No significant Degradation | No significant Degradation | No significant Degradation | | No significant Degradation |
| TUDCA API | % TUDCA | 95.1 | 97.2 | 82.8 | 96.4 | 99.5 |
| | % TUDCA remaining | 94.9 | 97.0 | 82.6 | | 103.2 |
| | TUDCA Peak Purity | Fail | Fail | Fail | Fail | Fail |
| | Conclusion | ~5% degradation | ~3% degradation | ~17% degradation | | No significant Degradation |
| Placebo | % PB | ND | ND | ND | ND | ND |
| | % TUDCA | ND | ND | ND | ND | ND |
| | Conclusion | Causes no interference at retention time of actives | Causes no interference at retention time of actives | Causes no interference at retention time of actives | | Causes no interference at retention time of actives |
| AMX-0035 Powder in Sachet | % PB | 99.0 | 98.9 | 99.2 | 99.2 | 99.6 |
| | % TUDCA | 97.4 | 96.4 | 97.1 | 93.8 | 97.1 |
| | % PB remaining | 99.9 | 99.8 | 100.1 | | 100.4 |
| | % TUDCA remaining | 100.2 | 99.2 | 99.9 | | 100.3 |
| | PB Peak Purity | Pass | Pass | Pass | Pass | Pass |
| | TUDCA Peak Purity | Fail | Fail | Fail | Fail | Fail |
| | Conclusion | No significant Degradation | No significant Degradation | No significant Degradation | | No significant Degradation |

*Two additional samples were prepared and analyzed after 3 and 7 days of exposure to the same Thermal-Humidity condition (85° C. with 1.0 mL water). The results confirmed that TUDCA samples fully degrade in the exposed condition. Only 1.30% TUDCA was detected in Day 3 sample (Ref: PDS-NB-16454 pg. 019).

TABLE 51

| Sample | Results | Control | Thermal | Thermal-Humidity | Oxidation | Acid 3 Days | Base 3 Days | Acid 7 Days | Base 7 Days | Light Control | Light |
|---|---|---|---|---|---|---|---|---|---|---|---|
| PB API | % Potency | 99.2 | 98.9 | 99.3 | 98.6 | 99.1 | 98.9 | 99.7 | 99.8 | 99.0 | 98.3 |
| | % Total RS | 2.07 | 3.93 | 1.16 | 3.13 | 1.18 | 1.11 | 1.14 | 1.10 | 0.96 | 0.74 |
| | Mass Balance | 101.27 | 102.83 | 100.48 | 101.73 | 100.28 | 100.01 | 100.84 | 100.90 | 99.96 | 99.04 |
| | % RMBD | N/A | 101.5 | 99.2 | 100.5 | 99.0 | 98.8 | 99.6 | 99.6 | N/A | 99.1 |
| TUDCA API | % Potency | 100.2 | 100.6 | ND | 97.1 | 100.0 | 95.1 | 97.2 | 82.8 | 96.4 | 99.5 |
| | % Total RS | 0.22 | 0.28 | ND | 1.36 | 0.23 | 0.22 | 0.20 | 0.18 | 0.22 | 0.24 |
| | Sum | 100.42. | 100.88 | 0.00 | 98.46 | 100.23 | 95.32 | 97.40 | 82.98 | 96.62 | 99.74 |
| | % RMBD | N/A | 100.5 | 0.0 | 98.8 | 99.8 | 94.9 | 97.0 | 82.6 | N/A | 103.2 |
| AMX-0035 Powder in Sachel | % PB Potency | 99.1 | 90.8 | 94.7 | 98.5 | 98.9 | 99.0 | 98.9 | 99.2 | 99.2 | 99.6 |
| | % Total PB Impurity | 0.78 | 12.12 | 2.90 | 2.01 | 1.14 | 2.28 | 1.10 | 2.42 | 0.86 | 0.81 |
| | PB Sum | 99.88 | 102.92 | 97.60 | 100.51 | 100.04 | 101.28 | 100.0 | 101.62 | 100.06 | 100.41 |
| | % RMBD | N/A | 103.0 | 97.7 | 100.6 | 100.2 | 101.4 | 100.1 | 101.7 | N/A | 100.3 |
| | % TUDCA Potency | 97.2 | 78.4 | 87.1 | 95.2 | 96.1 | 97.4 | 96.4 | 97.1 | 96.8 | 97.1 |
| | % Total TUDCA Impurity | 1.19 | 1.33 | 1.20 | 1.64 | 1.31 | 1.19 | 1.31 | 1.20 | 1.21 | 1.18 |
| | TUDCA Sum | 98.38 | 79.73 | 88.30 | 96.84 | 97.41 | 98.59 | 97.71 | 98.30 | 98.01 | 98.28 |
| | % RMBD | N/A | 81.0 | 89.7 | 98.4 | 99.0 | 100.2 | 99.3 | 99.9 | N/A | 100.3 |

Example 9: Effect of Cooling Unit on Blend Properties

Figure 15:
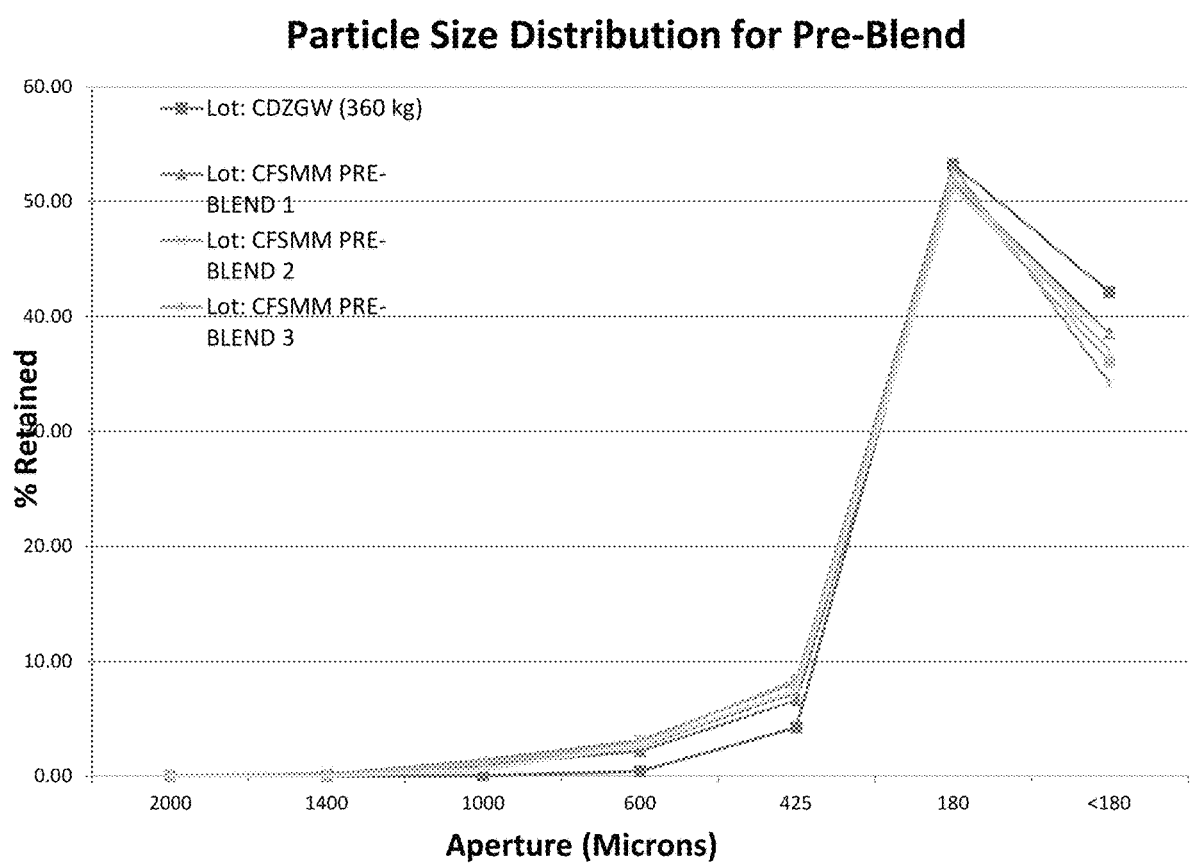
FIG. 15 shows the particle size distribution of the pre-blend for a placebo batch.
Figure 16:
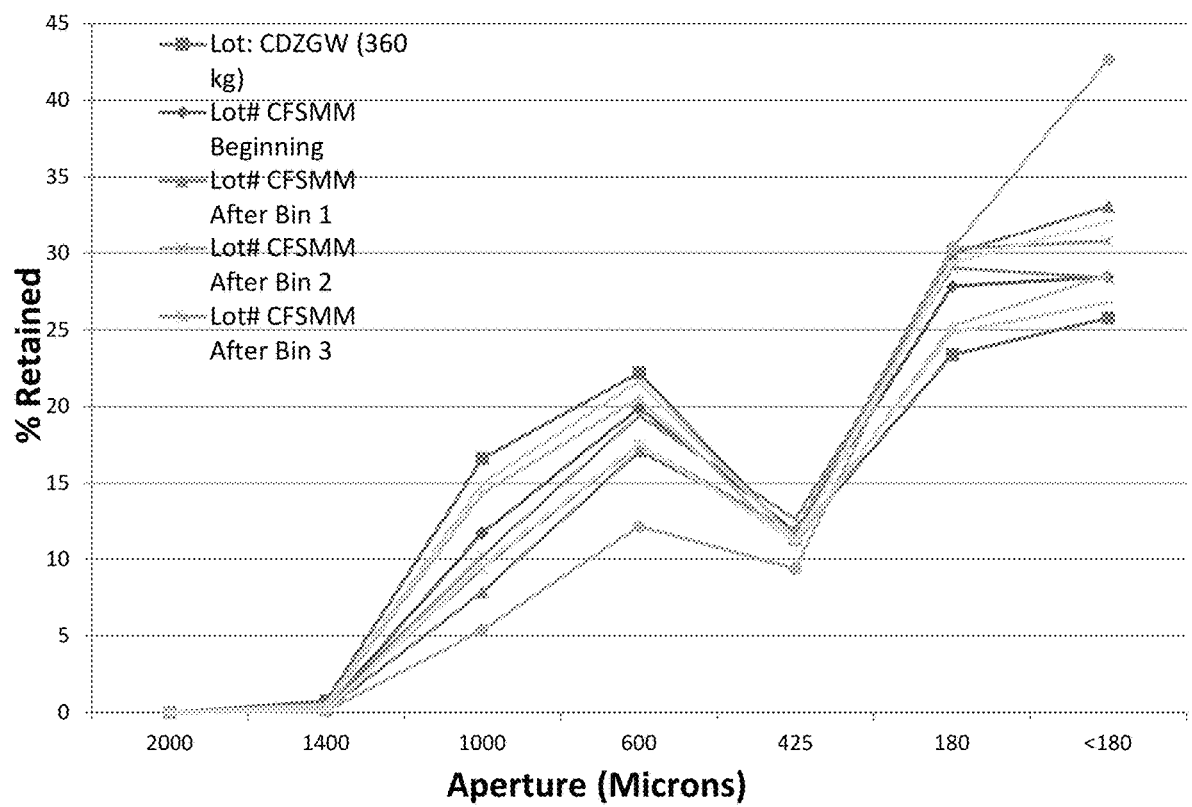
FIG. 16 shows the particle size distribution of the compacted granules for a placebo batch.

A placebo batch (Lot #CFSMM) was prepared where a cooling unit (15±2° C.) was added to the roller compactor. The temperature on the roller (nip area) during the entire batch was between 16.0-24.1° C. The temperature of the granules during the entire batch was between 24.8-29.0° C. No accumulation was observed on the rotary 1.5 mm screen during the entire batch. Table 52, 53, and FIGS. 15 and 16 show physical properties of the pre-blend and compacted granules. As shown in Table 53, compared to the flow index of lot CDZGW, which was prepared without the cooling unit, Lot CFSMM showed reduced flow index (i.e. improved flow properties). These results suggest that cooling the roller compactor can be beneficial for the processing conditions.

TABLE 52

Pre-blend results

Particle Size Distribution
Material: 100 grams of Pre-blend
% Retained

TRUE PLACEBO SCALE-UP - FEAS 2000 KG

| Mesh | Aperture (microns) | Placebo Lot: CDZGW (360 kg) | Lot: CFSMM PRE-BLEND 1 | Lot: CFSMM PRE-BLEND 2 | Lot: CFSMM PRE-BLEND 3 | Lot: CFSMM PRE-BLEND 4 | Lot: CFSMM PRE-BLEND 5 | Lot: CFSMM PRE-BLEND 6 |
|---|---|---|---|---|---|---|---|---|
| 10 | 2000 | 0.00 | 0.00 | 0.01 | 0.00 | 0.00 | 0.00 | 0.00 |
| 14 | 1400 | 0.00 | 0.08 | 0.20 | 0.13 | 0.05 | 0.00 | 0.00 |
| 18 | 1000 | 0.03 | 0.97 | 0.80 | 1.40 | 1.12 | 0.64 | 0.50 |
| 30 | 600 | 0.41 | 2.18 | 2.58 | 3.08 | 2.82 | 2.62 | 2.75 |
| 40 | 425 | 4.20 | 6.57 | 7.28 | 8.17 | 8.45 | 7.58 | 7.49 |
| 80 | 180 | 53.22 | 51.62 | 52.16 | 53.03 | 51.53 | 52.10 | 50.93 |
| PAN | <180 | 42.14 | 38.58 | 36.97 | 34.19 | 36.03 | 37.06 | 38.33 |
| Total | — | 100.00 | 100.00 | 100.00 | 100.00 | 100.00 | 100.00 | 100.00 |

Bulk and Tapped Density
Material: 100 grams of Pre-blend
Unit of Measurement: g/mL

TRUE PLACEBO SCALE-UP - FEAS 2000 KG

| | Placebo Lot: CDZGW (360 kg) | Lot: CFSMM PRE-BLEND 1 | Lot: CFSMM PRE-BLEND 2 | Lot: CFSMM PRE-BLEND 3 | Lot: CFSMM PRE-BLEND 4 | Lot: CFSMM PRE-BLEND 5 | Lot: CFSMM PRE-BLEND 6 |
|---|---|---|---|---|---|---|---|
| Bulk Density | 0.63 | 0.60 | 0.63 | 0.64 | 0.63 | 0.64 | 0.63 |
| Tapped Density | 0.83 | 0.78 | 0.81 | 0.78 | 0.79 | 0.81 | 0.81 |

Flow Index
Material: 50 grams of Pre-blend
Unit of Measurement: mm

AMX-0035 TRUE PLACEBO SCALE-UP - FEAS 2000 KG

| | Placebo Lot: CDZGW (360 kg) | Lot: CFSMM PRE-BLEND 1 | Lot: CFSMM PRE-BLEND 2 | Lot: CFSMM PRE-BLEND 3 | Lot: CFSMM PRE-BLEND 4 | Lot: CFSMM PRE-BLEND 5 | Lot: CFSMM PRE-BLEND 6 |
|---|---|---|---|---|---|---|---|
| Flow Index | 5 | 9 | 7 | 6 | 8 | 9 | 12 |

TABLE 53

Compacted granules results

Particle Size Distribution
Material: 100 grams of Compacted Granules
% Retained

AMX-0035 TRUE PLACEBO SCALE-UP - FEAS 2000 KG

| Mesh | Aperture (microns) | Placebo Lot: CDZGW (360 kg) | Lot # CFSMM Beginning | Lot # CFSMM After Bin 1 | Lot # CFSMM After Bin 2 | Lot # CFSMM After Bin 3 | Lot # CFSMM After Bin 4 | Lot # CFSMM After Bin 5 | Lot # CFSMM End | Lot # CFSMM Composite |
|---|---|---|---|---|---|---|---|---|---|---|
| 10 | 2000 | 0 | 0.00 | 0.00 | 0.00 | 0.00 | 0.00 | 0.00 | 0.00 | 0.00 |
| 14 | 1400 | 0.75 | 0.23 | 0.19 | 0.30 | 0.27 | 0.12 | 0.42 | 0.51 | 0.15 |
| 18 | 1000 | 16.60 | 11.72 | 7.85 | 10.22 | 9.42 | 5.39 | 14.33 | 14.99 | 9.60 |
| 30 | 600 | 22.20 | 19.92 | 17.10 | 19.42 | 17.49 | 12.15 | 20.57 | 21.66 | 17.61 |
| 40 | 425 | 11.31 | 11.83 | 11.82 | 12.64 | 11.75 | 9.38 | 10.88 | 11.25 | 11.17 |
| 80 | 180 | 23.38 | 27.85 | 29.95 | 29.04 | 30.29 | 30.34 | 25.25 | 24.82 | 29.36 |
| PAN | <180 | 25.76 | 28.45 | 33.09 | 28.38 | 30.78 | 42.62 | 28.55 | 26.77 | 32.11 |
| Total | — | 100.00 | 100.00 | 100.00 | 100.00 | 100.00 | 100.00 | 100.00 | 100.00 | 100.00 |

TABLE 53-continued

Compacted granules results

Bulk and Tapped Density
Material: 100 grams of Compacted Granules
Unit of Measurement: g/mL

AMX-0035 TRUE PLACEBO SCALE-UP - FEAS 2000 KG

|  | Placebo Lot: CDZGW (360 kg) | Lot # CFSMM Beginning | Lot # CFSMM After Bin 1 | Lot # CFSMM After Bin 2 | Lot # CFSMM After Bin 3 | Lot # CFSMM After Bin 4 | Lot # CFSMM After Bin 5 | Lot # CFSMM End | Lot # CFSMM Composite |
|---|---|---|---|---|---|---|---|---|---|
| Bulk Density | 0.63 | 0.68 | 0.67 | 0.65 | 0.66 | 0.68 | 0.67 | 0.67 | 0.68 |
| Tapped Density | 0.88 | 0.91 | 0.91 | 0.86 | 0.88 | 0.91 | 0.88 | 0.88 | 0.88 |

Flow Index
Material: 50 grams of Compacted Granules
Unit of Measurement: mm

AMX-0035 TRUE PLACEBO SCALE-UP - FEAS 2000 KG

|  | Placebo Lot: CDZGW (360 kg) | Lot # CFSMM Beginning | Lot # CFSMM After Bin 1 | Lot # CFSMM After Bin 2 | Lot # CFSMM After Bin 3 | Lot # CFSMM After Bin 4 | Lot # CFSMM After Bin 5 | Lot # CFSMM End | Lot # CFSMM Composite |
|---|---|---|---|---|---|---|---|---|---|
| Flow Index | 14 | 8 | 10 | 12 | 12 | 12 | 10 | 10 | 10 |

What is claimed is:

1. A composition comprising:
   (a) about 27% to about 32% w/w of sodium phenylbutyrate;
   (b) about 8% to about 12% w/w of taurursodiol (TURSO);
   (c) about 14% to about 17% w/w of dextrates;
   (d) about 3.5% to about 4.5% w/w of sorbitol;
   (e) about 25% to about 32% w/w of maltodextrin; and
   (f) about 0.05% to about 1.5% w/w of porous silica,
wherein the sodium phenylbutyrate and the TURSO have a ratio by weight of about 3:1, and wherein the composition has a measurable Carr's index of about 24 or less.

2. The composition of claim 1, comprising about 9% to about 10% w/w of TURSO.

3. The composition of claim 1, wherein the maltodextrin is pea maltodextrin.

4. The composition of claim 1, further comprising about 0.5% to about 5% w/w of sucralose.

5. The composition of claim 4, comprising about 1% to about 3% w/w of sucralose.

6. The composition of claim 1, further comprising about 2% to about 15% w/w of one or more flavorants.

7. The composition of claim 1, wherein the porous silica has an average pore volume of about 0.1 cc/gm to about 2.0 cc/gm.

8. The composition of claim 1, wherein the porous silica has a bulk density of about 100 g/L to about 600 g/L.

9. The composition of claim 1, further comprising about 0.5% to about 5% w/w of a buffering agent.

10. The composition of claim 9, wherein the buffering agent is sodium phosphate dibasic.

11. The composition of claim 10, comprising about 1% to about 4% w/w of sodium phosphate dibasic.

12. The composition of claim 1, further comprising about 0.05% to about 1% w/w of one or more lubricants.

13. The composition of claim 12, wherein the one or more lubricants are selected from the group consisting of: sodium stearyl fumarate, magnesium stearate, stearic acid, polyethylene glycol, glyceryl behenate, and hydrogenated oil.

14. The composition of claim 13, wherein the one or more lubricants is sodium stearyl fumarate.

15. The composition of claim 14, comprising about 0.2% to about 0.8% w/w of sodium stearyl fumarate.

16. The composition of claim 1, wherein the composition has a measurable Carr's index of about 20 or less.

17. The composition of claim 1, wherein the composition has a Carr's index of about 21.

18. The composition of claim 1, wherein the composition has a Carr's index of about 22.

19. The composition of claim 1, wherein the composition has a Carr's index of about 23.

20. The composition of claim 1, wherein the composition has a Carr's index of about 24.

21. A composition comprising:
   about 29.2% w/w of sodium phenylbutyrate;
   about 9.7% w/w of taurursodiol (TURSO);
   about 15.6% w/w of dextrates;
   about 3.9% w/w of sorbitol;
   about 1.9% w/w of sucralose;
   about 28.3% w/w of maltodextrin;
   about 7.3% w/w of flavorants;
   about 0.9% w/w of porous silica;
   about 2.7% w/w of sodium phosphate dibasic; and
   about 0.5% w/w of sodium stearyl fumarate,
   wherein the composition has a measurable Carr's index of about 24 or less.

* * * * *

UNITED STATES PATENT AND TRADEMARK OFFICE
CERTIFICATE OF CORRECTION

PATENT NO. : 11,583,542 B2
APPLICATION NO. : 16/940102
DATED : February 21, 2023
INVENTOR(S) : Joshua Cohen, Justin Klee and David Wai Fung Ma It is certified that error appears in the above-identified patent and that said Letters Patent is hereby corrected as shown below:

On the Title Page

Column 2, Line 13, delete "Drags" and insert -- Drugs --.

Column 2, Line 16, delete "16" and insert -- 10 --.

Signed and Sealed this
Twenty-fifth Day of April, 2023

Katherine Kelly Vidal
*Director of the United States Patent and Trademark Office*